(12) United States Patent
Sattarivand et al.

(10) Patent No.: US 12,376,812 B2
(45) Date of Patent: Aug. 5, 2025

(54) METHODS AND APPARATUS FOR DUAL ENERGY X-RAY IMAGING

(71) Applicant: DALHOUSIE UNIVERSITY, Halifax (CA)

(72) Inventors: Mike Sattarivand, Halifax (CA); Michael Reno, Halifax (CA)

(73) Assignee: DALHOUSIE UNIVERSITY, Halifax (CA)

( * ) Notice: Subject to any disclaimer, the term of this patent is extended or adjusted under 35 U.S.C. 154(b) by 820 days.

(21) Appl. No.: 17/252,682

(22) PCT Filed: May 6, 2019

(86) PCT No.: PCT/CA2019/050600
§ 371 (c)(1),
(2) Date: Dec. 15, 2020

(87) PCT Pub. No.: WO2019/237179
PCT Pub. Date: Dec. 19, 2019

(65) Prior Publication Data
US 2021/0267563 A1    Sep. 2, 2021

Related U.S. Application Data

(60) Provisional application No. 62/685,776, filed on Jun. 15, 2018.

(51) Int. Cl.
*A61B 6/00*    (2024.01)
*A61B 6/03*    (2006.01)
(Continued)

(52) U.S. Cl.
CPC .............. *A61B 6/482* (2013.01); *A61B 6/032* (2013.01); *A61B 6/40* (2013.01); *A61B 6/505* (2013.01);
(Continued)

(58) Field of Classification Search
CPC ........... A61B 6/482; A61B 6/032; A61B 6/40; A61B 6/505; A61B 6/5235; A61B 6/4035;
(Continued)

(56) References Cited

U.S. PATENT DOCUMENTS 4,792,900 A    12/1988    Sones et al.
5,841,833 A    11/1998    Mazess et al.
(Continued)

FOREIGN PATENT DOCUMENTS

DE    102011004120 B4    4/2017
EP    2548510 B1    12/2016
(Continued)

OTHER PUBLICATIONS

Seidlitz, J., Sponheim, C., Glen, D., Frank, Q.Y., Saleem, K.S., Leopold, D.A., Ungerleider, L. and Messinger, A., 2018. A population MRI brain template and analysis tools for the macaque. Neuroimage, 170, pp. 121-131.*
(Continued)

*Primary Examiner* — Zhitong Chen
(74) *Attorney, Agent, or Firm* — Todd A. Rattray; Oyen Wiggs Green & Mutala LLP

(57) ABSTRACT

Dual energy x-ray images may be generated by combining higher and lower energy images of a subject's tissue region with weighting factor values determined based on thicknesses of different tissue types corresponding to the imaged tissue region. Different weighting factor values may be applied to different pixels of the higher or lower energy images. Weighting factor values may, for example, be retrieved from memory, calculated, interpolated and/or extrapolated or the like. The higher and lower energy images and the weighting factor values may be linearly combined to generate a dual energy x-ray image. In some embodiments
(Continued)

the weighting factor values may increase contrast of a tissue type.

24 Claims, 22 Drawing Sheets

(51) Int. Cl.
  *A61B 6/40*    (2024.01)
  *A61B 6/50*    (2024.01)
  *G06T 5/50*    (2006.01)
  *G06T 5/70*    (2024.01)

(52) U.S. Cl.
  CPC .............. *A61B 6/5235* (2013.01); *G06T 5/50* (2013.01); *G06T 5/70* (2024.01); *G06T 2207/10116* (2013.01); *G06T 2207/30061* (2013.01); *G06T 2207/30096* (2013.01)

(58) Field of Classification Search
  CPC . G06T 5/002; G06T 5/50; G06T 2207/10116; G06T 2207/30061; G06T 2207/30096; G06T 2207/10016; A61N 5/1049; A61N 5/1067; A61N 5/107; A61N 2005/1061
  See application file for complete search history.

(56) References Cited

U.S. PATENT DOCUMENTS

| | | |
|---|---|---|
| 6,661,873 B2 | 12/2003 | Jabri et al. |
| 6,683,934 B1 | 1/2004 | Zhao et al. |
| 6,816,564 B2 | 11/2004 | Charles, Jr. et al. |
| 7,010,092 B2 | 3/2006 | Winsor |
| 7,068,826 B2 | 6/2006 | Jabri et al. |
| 7,627,084 B2 | 12/2009 | Jabri et al. |
| 7,873,141 B2 | 1/2011 | Imai et al. |
| 9,351,695 B2 | 5/2016 | Wang et al. |
| 9,492,134 B2 | 11/2016 | Takasaki |
| 9,662,078 B2 | 5/2017 | Berglund et al. |
| 9,693,742 B2 | 7/2017 | Grasruck et al. |
| 9,754,387 B2 | 9/2017 | Leng et al. |
| 9,820,712 B2 | 11/2017 | Takasaki |
| 9,886,765 B2 | 2/2018 | Naito |
| 9,905,003 B2 * | 2/2018 | Maack ................... A61B 6/482 |
| 2012/0082295 A1 | 4/2012 | Agano et al. |
| 2014/0219423 A1 | 8/2014 | Bertens |
| 2017/0116730 A1 | 4/2017 | Yamanaka |
| 2017/0000439 A1 | 11/2017 | Takasaki |
| 2018/0015306 A1 | 1/2018 | Maurer, Jr. et al. |
| 2018/0061088 A1 | 3/2018 | Bhagalia et al. |
| 2018/0068442 A1* | 3/2018 | Kawamura ........... G06T 7/0012 |

FOREIGN PATENT DOCUMENTS

| | | |
|---|---|---|
| EP | 2243020 B1 | 9/2017 |
| EP | 3287774 A1 | 2/2018 |
| JP | 05-236351 A | 9/1993 |
| JP | 07-85247 A | 3/1995 |
| JP | 2002-152593 A | 5/2002 |
| JP | 2007-044520 A | 2/2007 |
| JP | 4526110 B2 | 8/2010 |
| JP | 2010-194261 A | 9/2010 |
| JP | 2013-85967 A | 5/2013 |
| JP | 5680718 B2 | 3/2015 |
| JP | 6129125 B2 | 5/2017 |
| JP | 2017-122705 A | 7/2017 |
| JP | 6242631 B2 | 12/2017 |
| JP | 6261915 B2 | 1/2018 |
| JP | 2018-015664 A | 2/2018 |
| JP | 6275374 B2 | 2/2018 |
| JP | 2018-506385 A | 3/2018 |
| KR | 101848177 B1 | 4/2018 |
| WO | 2013037659 A1 | 3/2013 |
| WO | 2016168194 A1 | 10/2016 |
| WO | 2018005721 A1 | 1/2018 |

OTHER PUBLICATIONS

Wan Y, Hu H, Xu Y, Chen Q, Wang Y, Gao D. A Robust and Accurate Non-rigid Medical Image Registration Algorithm Based on Multi-level Deformable Model. Iran J Public Health. Dec. 2017;46(12):1679-1689. PMID: 29259943; PMCID: PMC5734968.*

Alvarez, R. E. et al., "Energy-Selective Reconstructions in X-Ray Computerized Tomography", Physics in Medicine and Biology 21(5):733-744, 1976.

Ay, M. R. et al., "Assessment of Different Computational Models for Generation of X-Ray Spectra in Diagnostic Radiology and Mommography", Med Phys 32:1660-1675, 2006.

Bowman, W. A. et al., "Optimizing Dual-Energy X-Ray Parameters for the ExacTrac Clinical Stereoscopic Imaging System to Enhance Soft-Tissue Imaging", Medical Physics 44(3):823-831, doi:10.1002/mp.12093, 2017.

Burton, C. S. et al., "Energy Subtraction Angiography is Comparable to Digital Subtraction Angiography in Terms of Iodine Rose SNR", Medical Physics 43(11):5925, doi:10.1118/1.4962651, 2016.

Dhont, J., D. et al., "Feasibility of Markerless Tumor Tracking by Sequential Dual-Energy Fluoroscopy on a Clinical Tumor Tracking System", Radiotherapy and Oncology: Journal of the European Society for Therapeutic Radiology and Oncology 117(3):487-490, doi:10.1016/j.radonc.2015.08.021, 2015.

Ducote, J. L. et al., "Optimization of a Flat-Panel Based Real Time Dual-Energy System for Cardiac Imaging", Medical Physics 33(6):1562-1568, doi:10.1118/1.2174131, 2006.

Ergun, D. L. et al., "Single-Exposure Dual-Energy Computed Radiography: Improved Detection and Processing", Radiology 174(1):243-249, doi:10.1148/radiology.174.1.2294555, 1990.

Fischbach, F. et al., "Dual-Energy Chest Radiography with a Flat-Panel Digital Detector: Revealing Calcified Chest Abnormalities", AJR, AM. J. Roentgenol. 181:1519-1524, 2003.

Ho, J. T. et al., "Comparison of Dual and Single Exposure Techniques in Dual-Energy Chest Radiography", Medical Physics 16(2):202-208, doi:10.1118/1.596372, 1989.

Hoggarth, M. A. et al., "Dual Energy Imaging using a Clinical on-Board Imaging System", Physics in Medicine and Biology 58(12):4331-4340, doi:10.1088/0031-9155/58/12/4331, 2013.

Kalender, W. A. et al., "An Algorithm for Noise Suppression in Dual Energy CT Material Density Images", IEEE Transactions on Medical Imaging 7(3):218-224, doi:10.1109/42.7785, 1988.

Karunamuni, R. et al., "Search for Novel Contrast Materials in Dual-Energy X-Ray Breast Imaging using Theoretical Modeling of Contrast-to-Noise Ratio", Physics in Medicine and Biology 59(15):4311-4324, doi:10.1088/0031-9155/59/15/4311, 2014.

Lehmann, L. A. et al., "Generalized Image Combinations in Dual KVP Digital Radiography", Medical Physics 8:659-667, 1981.

Li, H. et al., "Implementation of Dual-Energy Technique for Virtual Monochromatic and Linearly Mixed CBCTs", Medical Physics 39(10):6056-6064, doi:10.1118/1.4752212, 2012.

McCollough, C. H. et al., "A Correlated Noise Reduction Algorithm for Dual-Energy Digital Subtraction Angiography", Medical Physics 16(6):873-880, doi:10.1118/1.596436, 1989.

Menten, M. J. et al., "Using Dual-Energy X-Ray Imaging to Enhance Automated Lung Tumor Tracking during Real-Time Adaptive Radiotherapy", Medical Physics 42(12):6987-6998, doi:10.1118/1.4935431, 2015.

Molloi, S. Y. et al., "Quantification Techniques for Dual-Energy Cardiac Imaging", Medical Physics 16(2):209-217, doi:10.1118/1.596418, 1989.

Rebuffel, V. et al., "Dual-Energy X-Ray Imaging: Benefits and Limits", Ecndt 49:1-12, 2006.

Richard, S. et al., "Cascaded Systems Analysis of Noise Reduction Algorithms in Dual-Energy Imaging", Medical Physics 35(2):586-601, doi:10.1118/1.2826556, 2008.

Richard, S. et al., "Optimization of Dual-Energy Imaging Systems using Generalized NEQ and Imaging Task", Medical Physics 34(1):127-139, doi:10.1118/1.2400620, 2007.

Sabol, J. et al., "Simulated and Experimental Technique Optimization of Dual-Energy Radiography: Abdominal Imaging Applications", Medical Imaging 6142:545-556, 2006.

(56) References Cited

OTHER PUBLICATIONS

Saito, M. et al., "A Simple Formulation for Deriving Effective Atomic Numbers Via Electron Density Calibration from Dual-Energy CT Data in the Human Body", Medical Physics (44):2293-2303, 2017.

Shkumat, N. A. et al., "Optimization of Image Acquisition Techniques for Dual-Energy Imaging of the Chest", Medical Physics 34(10):3904-3915, doi:10.1118/1.2777278, 2007.

Siddon, R. L. "Fast Calculation of the Exact Radiological Path for a Three-Dimensional CT Array", Medical Physics 12(2):252-255, doi:10.1118/1.595715, 1985.

Szucs-Farkas, Z. et al., "Single-Exposure Dual-Energy Subtraction Chest Radiography: Detection of Pulmonary Nodules and Masses in Clinical Practice", European Radiology 18(1):24-31, doi:10.1007/s00330-007-0758-z, 2008.

Vock, P. et al., "Dual Energy Subtraction: Principles and Clinical Applications", European Journal of Radiology 72(2):231-237, doi:10.1016/j.ejrad.2009.03.046, 2009.

Williams, D. B. et al., "Optimal kVp Selection for Dual-Energy Imaging of the Chest: Evaluation by Task-Specific Observer Preference Tests", Medical Physics 34(10):3916-3925, doi:10.1118/1.2776239, 2007.

Xu, T. et al., "Dynamic Dual-Energy Chest Radiography: A Potential Tool for Lung Tissue Motion Monitoring and Kinetic Study", Physics in Medicine and Biology 56(4):1191-1205, doi:10.1088/0031-9155/56/4/019, 2011.

Yu, L. et al., "Virtual Monochromatic Imaging in Dual-Source Dual-Energy CT: Radiation Dose and Image Quality", Medical Physics 38:6371-6379, 2011.

"Dual Energy Radiography Acquisition and Processing", SUNY Upstate Medical University, http://www.upstate.edu/radiology/education/rsna/radiography/dual.php, Mar. 14, 2018.

Schmidt, T., "Optimal 'image-based' weighting for energy-resolved CT", Med. Phys. 36(7):3018-27, doi:10.1118/1.3148535, 2009.

Cruz-Bastida, J.-P. et al., Contrast Optimization in Clinical Contrast-Enhanced Digital Mammography Images. In: Maidment A.D.A., Bakic P.R., Gavenonis S. (eds) Breast Imaging. IWDM 2012. Lecture Notes in Computer Science, vol. 7361. Springer, Berlin, Heidelberg. https://doi.org/10.1007/978-3-642-31271-7_3 (2012).

Vijayakumar, S. et al., "Beam's Eye View-based Radiation Therapy: Description of Methods", RadioGraphics 1992; 12:961-968.

\* cited by examiner

METHODS AND APPARATUS FOR DUAL ENERGY X-RAY IMAGING

CROSS-REFERENCE TO RELATED APPLICATION

This application claims the benefit under 35 U.S.C. § 119 of U.S. Application No. 62/685,776 filed 15 Jun. 2018 and entitled METHODS AND APPARATUS FOR DUAL ENERGY X-RAY IMAGING which is hereby incorporated herein by reference for all purposes.

TECHNICAL FIELD

This invention relates to medical imaging and, in particular, to dual energy x-ray imaging.

BACKGROUND

Image-guided radiation therapy (IGRT) is a technique that involves acquiring images during a course of radiation therapy. IGRT can deliver radiation with improved accuracy by taking into account changes in a subject as revealed by the images. Images may be taken before or during the delivery of radiation. Some radiation sources, such as linear accelerators are equipped with imaging systems such as kV X-ray imagers for acquiring images of a subject while the subject is positioned for the delivery of radiation.

Anatomical noise can interfere with obtaining clear images of anatomical structures in IGRT. For example, in lung stereotactic body radiation therapy (SBRT), a type of IGRT, rib bones may obscure the detection and/or monitoring of lung tumors.

Dual energy x-ray imaging exploits the fact that x-rays of different energies are attenuated differently by different tissue types (e.g. tissues having different densities). Dual energy x-ray imaging involves acquiring a higher energy x-ray image and a lower energy x-ray image. The higher energy x-ray image and the lower energy x-ray image can be combined to generate images in which certain tissue types are emphasized or de-emphasized. Using dual energy x-ray imaging, it is possible to produce images in which a selected structure is emphasized while tissues which attenuate radiation differently from the selected structure are de-emphasized. For example, known dual energy x-ray imaging methods may be used to generate images of a subject's thorax in which the contribution of bone to the images is de-emphasized.

The use of dual energy x-ray imaging is not limited to IGRT applications. Dual energy x-ray imaging can also be useful in diagnostic imaging applications, surveillance applications (e.g. x-ray screening of contents of baggage, etc.) or the like.

There is a general desire for novel methods and apparatus which generate dual energy x-ray images which may emphasize or de-emphasize one or more imaged tissue types (e.g. bone tissue, soft tissue or the like).

A wide range of approaches to dual energy x-ray imaging have been discussed in the academic and patent literature. Some examples are described in the following publications:
1. Alvarez, R. E. and A. Macovski. 1976. "Energy-Selective Reconstructions in X-Ray Computerized Tomography." Physics in Medicine and Biology 21 (5): 733-744.
2. Ay M. R., Sarkar S., Shahriari M., Sardari D., and Zaidi H. 2006. "Assessment of Different Computational Models for Generation of X-Ray Spectra in Diagnostic Radiology and Mommography." Med Phys 32: 1660-1675.
3. Bowman, W. A., J. L. Robar, and M. Sattarivand. 2017. "Optimizing Dual-Energy X-Ray Parameters for the ExacTrac Clinical Stereoscopic Imaging System to Enhance Soft-Tissue Imaging." Medical Physics 44 (3): 823-831. doi:10.1002/mp.12093.
4. Burton, C. S., J. R. Mayo, and I. A. Cunningham. 2016. "Energy Subtraction Angiography is Comparable to Digital Subtraction Angiography in Terms of Iodine Rose SNR." Medical Physics 43 (11): 5925. doi:10.1118/1.4962651.
5. Dhont, J., D. Verellen, K. Poels, K. Tournel, M. Burghelea, T. Gevaert, C. Collen, et al. 2015. "Feasibility of Markerless Tumor Tracking by Sequential Dual-Energy Fluoroscopy on a Clinical Tumor Tracking System." Radiotherapy and Oncology: Journal of the European Society for Therapeutic Radiology and Oncology 117 (3): 487-490. doi:10.1016/j.radonc.2015.08.021.
6. Ducote, J. L., T. Xu, and S. Molloi. 2006. "Optimization of a Flat-Panel Based Real Time Dual-Energy System for Cardiac Imaging." Medical Physics 33 (6): 1562-1568. doi:10.1118/1.2174131.
7. Ergun, D. L., C. A. Mistretta, D. E. Brown, R. T. Bystrianyk, W. K. Sze, F. Kelcz, and D. P. Naidich.1990. "Single-Exposure Dual-Energy Computed Radiography: Improved Detection and Processing." Radiology 174 (1): 243-249. doi:10.1148/radiology.174.1.2294555.
8. Fischbach, F., T. Freund, R. Rottgen, U. Engert, R. Felix, and J. Ricke. 2003. "Dual-Energy Chest Radiography with a Flat-Panel Digital Detector: Revealing Calcified Chest Abnormalities." AJR, AM. J. Roentgenol. 181: 1519-1524.
9. Ho, J. T., R. A. Kruger, and J. A. Sorenson. 1989. "Comparison of Dual and Single Exposure Techniques in Dual-Energy Chest Radiography." Medical Physics 16 (2): 202-208. doi:10.1118/1.596372.
10. Hoggarth, M. A., J. Luce, F. Syeda, T. S. Bray, A. Block, S. Nagda, and J. C. Roeske. 2013. "Dual Energy Imaging using a Clinical on-Board Imaging System." Physics in Medicine and Biology 58 (12): 4331-4340. doi:10.1088/0031-9155/58/12/4331.
11. Kalender, W. A., E. Klotz, and L. Kostaridou. 1988. "An Algorithm for Noise Suppression in Dual Energy CT Material Density Images." IEEE Transactions on Medical Imaging 7 (3): 218-224. doi:10.1109/42.7785.
12. Karunamuni, R. and A. D. Maidment. 2014. "Search for Novel Contrast Materials in Dual-Energy X-Ray Breast Imaging using Theoretical Modeling of Contrast-to-Noise Ratio." Physics in Medicine and Biology 59 (15): 4311-4324. doi:10.1088/0031-9155/59/15/4311.
13. Lehmann L. A., Alvarez R. E., Macovski A., and Brody W. R. 1981. "Generalized Image Combinations in Dual KVP Digital Radiography." Medical Physics 8: 659-667.
14. Li, H., W. Giles, L. Ren, J. Bowsher, and F. F. Yin. 2012. "Implementation of Dual-Energy Technique for Virtual Monochromatic and Linearly Mixed CBCTs." Medical Physics 39 (10): 6056-6064. doi:10.1118/1.4752212.
15. McCollough, C. H., M. S. Van Lysel, W. W. Peppler, and C. A. Mistretta. 1989. "A Correlated Noise Reduction Algorithm for Dual-Energy Digital Subtraction Angiography." Medical Physics 16 (6): 873-880. doi:10.1118/1.596436.
16. Menten, M. J., M. F. Fast, S. Nill, and U. Oelfke. 2015. "Using Dual-Energy X-Ray Imaging to Enhance Automated Lung Tumor Tracking during Real-Time Adaptive Radiotherapy." Medical Physics 42 (12): 6987-6998. doi: 10.1118/1.4935431.

17. Molloi, S. Y. and C. A. Mistretta. 1989. "Quantification Techniques for Dual-Energy Cardiac Imaging." Medical Physics 16 (2): 209-217. doi:10.1118/1.596418.
18. Rebuffel, V. and J. M. Dinten. 2006. "Dual-Energy X-Ray Imaging: Benefits and Limits." Ecndt 49: 1-12.
19. Richard, S. and J. H. Siewerdsen. 2008. "Cascaded Systems Analysis of Noise Reduction Algorithms in Dual-Energy Imaging." Medical Physics 35 (2): 586-601. doi:10.1118/1.2826556.
20. 2007. "Optimization of Dual-Energy Imaging Systems using Generalized NEQ and Imaging Task." Medical Physics 34 (1): 127-139. doi:10.1118/1.2400620.
21. Sabol, J., S. Wheeldon, and S. K. Thompson. 2006. "Simulated and Experimental Technique Optimization of Dual-Energy Radiography: Abdominal Imaging Applications." Medical Imaging 6142: 545-556.
22. Saito, M. and S. Sagara. 2017. "A Simple Formulation for Deriving Effective Atomic Numbers Via Electron Density Calibration from Dual-Energy CT Data in the Human Body." Medical Physics (44): 2293-2303.
23. Shkumat, N. A., J. H. Siewerdsen, A. C. Dhanantwari, D. B. Williams, S. Richard, N. S. Paul, J. Yorkston, and R. Van Metter. 2007. "Optimization of Image Acquisition Techniques for Dual-Energy Imaging of the Chest." Medical Physics 34 (10): 3904-3915. doi:10.1118/1.2777278.
24. Szucs-Farkas, Z., M. A. Patak, S. Yuksel-Hatz, T. Ruder, and P. Vock. 2008. "Single-Exposure Dual-Energy Subtraction Chest Radiography: Detection of Pulmonary Nodules and Masses in Clinical Practice." European Radiology 18 (1): 24-31. doi:10.1007/s00330-007-0758-z.
25. Vock, P. and Z. Szucs-Farkas. 2009. "Dual Energy Subtraction: Principles and Clinical Applications." European Journal of Radiology 72 (2): 231-237. doi:10.1016/j.ejrad.2009.03.046.
26. Williams, D. B., J. H. Siewerdsen, D. J. Tward, N. S. Paul, A. C. Dhanantwari, N. A. Shkumat, S. Richard, J. Yorkston, and R. Van Metter. 2007. "Optimal Kvp Selection for Dual-Energy Imaging of the Chest: Evaluation by Task-Specific Observer Preference Tests." Medical Physics 34 (10): 3916-3925. doi:10.1118/1.2776239.
27. Xu, T., J. L. Ducote, J. T. Wong, and S. Molloi. 2011. "Dynamic Dual-Energy Chest Radiography: A Potential Tool for Lung Tissue Motion Monitoring and Kinetic Study." Physics in Medicine and Biology 56 (4): 1191-1205. doi:10.1088/0031-9155/56/4/019.
28. Yu, L., J. A. Christner, S. Leng, J. Wang, and J. G. Fletcher. 2011. "Virtual Monochromatic Imaging in Dual-Source Dual-Energy CT: Radiation Dose and Image Quality." Medical Physics 38: 6371-6379.
29. U.S. Pat. No. 6,683,934.
30. U.S. Pat. No. 9,351,695.
31. US 2014/0219423.
32. US 2018/0015306.
33. US 2017/0116730.
34. US 2012/0082295.
35. DE 102011004120.
36. EP 2,243,020.
37. EP 2,548,510.
38. EP 3,287,774.
39. JP 4526110.
40. JP 05236351.
41. JP 07085247.
42. JP 5680718.
43. JP 6129125.
44. JP 6242631.
45. JP 6261915.
46. JP 6275374.
47. JP 2007-44520.
48. JP 2017-122705.
49. JP 2018-015664.
50. JP 2018-506385.
51. U.S. Pat. No. 4,792,900.
52. U.S. Pat. No. 5,841,833.
53. U.S. Pat. No. 6,661,873.
54. U.S. Pat. No. 6,816,564.
55. U.S. Pat. No. 7,068,826.
56. U.S. Pat. No. 7,627,084.
57. U.S. Pat. No. 7,873,141.
58. U.S. Pat. No. 9,492,134.
59. U.S. Pat. No. 9,662,078.
60. U.S. Pat. No. 9,693,742.
61. U.S. Pat. No. 9,754,387.
62. U.S. Pat. No. 9,886,765.
63. U.S. Pat. No. 9,905,003.
64. US 2018/0061088.
65. US 2018/0068442.
66. WO 2016/168194.
67. WO 2018/005721.

The foregoing examples of the related art and limitations related thereto are intended to be illustrative and not exclusive. Other limitations of the related art will become apparent to those of skill in the art upon a reading of the specification and a study of the drawings.

SUMMARY

This invention has a number of aspects. These include, without limitation:
  methods for dual energy x-ray imaging;
  methods and apparatus for determining thicknesses of tissue corresponding to one or more pixels of an x-ray image;
  methods and apparatus for image guided therapies;
  methods and apparatus for defining image weighting values;
  methods and apparatus for producing images in which one or more tissue types is de-emphasized and/or contrast of one or more tissue types is increased; and
  dual energy x-ray imaging systems.

One aspect of the invention provides methods for dual energy x-ray imaging. The methods comprise acquiring first and second images of a tissue region comprising a first tissue type having a first density and a second tissue type having a second density. The first image corresponds to a first radiation beam having a first energy spectrum and the second image corresponds to a second radiation beam having a second energy spectrum different from the first energy spectrum. The methods comprise combining the first and second images to generate a combined image by, separately for each of multiple parts of the first and second images, determining a weighting factor corresponding to the part and pixelwise combining the first and second images using the weighting factors to yield a combined image. The parts of the images for which weighting factors are generated may be individual pixels or areas that include more than one pixel.

In some embodiments the first and second radiation beams are x-ray beams.

$^L$ In some embodiments the first energy spectrum has a maximum energy higher than a maximum energy of the second energy spectrum.

In some embodiments the first energy spectrum has an average photon energy greater than an average photon energy of the second energy spectrum.

In some embodiments combining the first and second images comprises computing a linear weighted difference of pixel values in the first and second images or computing a weighted difference of logarithms of pixel values in the first and second images. For example, computing the weighted difference of logarithms of pixels values in the first and second images may comprise performing the computation:

$$\ln(I_{DE}) = \ln(I_{HE}) - \omega \ln(I_{LE}),$$

or a mathematical equivalent thereof, wherein $I_{HE}$ represents pixel values in the first image, $I_{LE}$ represents pixel values in the second image, $\omega$ represents the weighting factors and $I_{DE}$ represents pixel values in the combined image.

In some embodiments combining the first and second images comprises registering the first and second images by applying one or more transformations to one or both of the first and second images. Registering the first and second images may comprises transforming one or both of the first and second images to align pixels of the first image with corresponding pixels of the second image. The transformations may be rigid transformations (i.e. transformations that do not change relative positions of the pixels in the image being transformed) and/or non-rigid transformations (i.e. transformations in which different parts of an image are differently scaled and/or rotated and/or transformations in which angles formed by groups of three pixels are not preserved). The one or more transformations may, for example comprise at least one of displacing one of the first and second images relative to the other one of the first and second images, rotating one of the first and second image relative to the other one of the first and second images and scaling one of the first and second image relative to the other one of the first and second images.

In some embodiments determining the weighting factors comprises determining a thickness of tissue of each of at least two classes corresponding to each of the parts of the first and second images. This may be done in a variety of ways including: computing the thicknesses from pixel values in the first and second images, computing the thicknesses by processing volumetric data (e.g. a CT or MRI scan), direct measurement of tissue thicknesses etc. In some embodiments the method comprises processing CT data to classify voxels of the CT data into the at least two classes based on densities indicated by the CT data for the voxels, generating a volumetric mask for each of the at least two classes, each volumetric mask comprising data indicating for voxels of the volumetric mask whether the voxel does or does not correspond to tissue of the corresponding class, and processing the volumetric masks. Processing the volumetric masks may, for example comprise computing digitally reconstructed radiographs (DRRs) for each of the volumetric masks from the point of view of the first and second images. The processing of the volumetric masks may be based on a geometry of the first and second radiation beams and may comprise determining the thickness of tissue of each of the at least two classes along rays of the first and second radiation beams corresponding to pixels of the first and second images.

The weighting factors may be determined based on the tissue thicknesses. This may be done in any of a variety of ways including: computation of the weighting factors, and/or using the thicknesses to look up predetermined weighting factors.

In some embodiments the methods comprise using the thickness of tissue of each of at least two classes as keys to retrieve the weighting factor for each of the parts from a lookup table. The lookup table optionally comprises a plurality of reference weighting factors. In some embodiments the plurality of reference weighting factors comprises a first set of weighting factors selected to de-emphasize tissue of a first one of the at least two classes in the combined image and a second set of weighting factors configured to de-emphasize tissue of a second one of the at least two classes in the combined image. For example the lookup table may comprise a set of weighting factors that increases contrast of tumor tissue in the combined image.

In some embodiments retrieving the weighting factor from the lookup table comprises one or more of interpolating and extrapolating the weighting factor from the plurality of reference weighting values. The reference weighting factors may be determined, for example by calculation and/or by experiments in which different thicknesses of tissue mimicking materials are imaged. Non-limiting examples of such experiments are provided in the detailed description.

In some embodiments the first radiation beam is generated using a peak x-ray tube voltage greater than 80 kVp and the second radiation beam is generated using a peak x-ray tube voltage lower than the peak x-ray tube voltage used to generate the first radiation bean and less than 100 kVp. For example:
  the first radiation beam may be generated using a peak x-ray tube voltage of 120±25 kVp; and/or
  the second radiation beam may be generated using a peak x-ray tube voltage of 80±25 kVp; and/or
  the method may comprise filtering one or both of the first and second radiation beams.

In some embodiments the first radiation beam is filtered and the filtering of the first radiation beam hardens the first radiation beam. In some embodiments the second radiation beam is filtered and the filtering of the second radiation beam softens the second radiation beam. In some embodiments for at least one of the first and second radiation beams, the filtering comprises passing the radiation beam through first and second materials. For example, the first radiation beam may be passed through an aluminum filter and a holmium filter and/or the second radiation beam may be passed through an aluminum filter and a copper filter.

In some embodiments:
  bone tissue in the combined image has a contrast lower than a contrast of bone tissue in either of the first and second images and/or
  soft tissue in the combined image has a contrast lower than a contrast of soft tissue in either of the first and second images and/or
  tumor tissue in the combined image has a contrast greater than a contrast of tumor tissue in either of the first and second images.

In some embodiments the methods comprise identifying a region of interest and determining the weighting factors comprises: for pixels within the region of interest selecting the weighting factors that cause increased contrast for a first selected tissue type; and for pixels outside of the region of interest selecting the weighting factors that cause de-emphasis for a second selected tissue type. For example, the first selected tissue type may correspond to soft tissue having a first density range and/or the first density range is a density range characteristic of tumors in the tissue region and/or the second selected tissue type corresponds to bone tissue.

In some embodiments determining the weighting factors comprises: for pixels within the region of interest using a first algorithm to determine the weighting factors; and for pixels outside of the region of interest using a second algorithm different from the first algorithm to determine the weighting factors. The first and second algorithms may have different goals such as de-emphasizing different tissue types and/or enhancing contrast for one tissue type and de-emphasizing another tissue type and/or enhancing contrast for different tissue types.

In some embodiments determining the weighting factors comprises: for pixels within the region of interest selecting weighting factors from a first set of weighting factors; and for pixels outside of the region of interest selecting the weighting factors from a second set of weighting factors. In some embodiments two or more sets of weighting factors are generated (these may be provided in the form of weighting factor images) and different regions in the combined images are created using different ones of the sets of weighting factors.

In embodiments which determine weighting factors for region of interest in a different way than for outside of the region of interest weighting factors for pixels in a margin along a boundary of the region of interest may be determined by blending weighting factors of two sets (e.g. blending weighting factors that cause increased contrast for a first selected tissue type and weighting factors that cause de-emphasis for a second selected tissue type).

In some embodiments identifying the region of interest comprises receiving user input and/or setting the region of interest to encompass tumors identified in volumetric data of the tissue region.

Another aspect of the invention provides x-ray imaging methods comprising: acquiring a first image of a tissue region by controlling a radiation source to emit a first radiation beam having a first energy range; acquiring a second image of the tissue region by controlling the radiation source to emit a second radiation beam having a second energy range wherein a maximum energy of the second energy range is lower than a maximum energy of the first energy range; determining amounts of tissue in plural density ranges lying on rays extending between the radiation source and locations on a detector used to acquire pixels of the first and second images and determining weighting factors for the pixels based on the amounts; and pixelwise combining the first and second images to generate a combined image by, separately for each pixel of the combined image, combining corresponding pixels of the first and second images using the corresponding one of the weighting factors.

In some embodiments:
the plural density ranges comprise a density range corresponding to bone; and/or
the method comprises classifying tissues having a density greater than a threshold density in one of the plural density ranges and classifying tissues having density less than the threshold density in a second one of the plural density ranges; and/or
combining the first and second images comprises computing a weighted difference of logarithms of pixel values in the first and second images; and/or.
computing the weighted difference of logarithms of pixels values in the first and second images comprises performing the computation:

$$\ln(I_{DE}) = \ln(I_{HE}) - \omega \ln(I_{LE}),$$

or a mathematical equivalent thereof, wherein $I_{HE}$ represents pixel values in the first image, $I_{LE}$ represents pixel values in the second image, $\omega$ represents the weighting factors and $I_{DE}$ represents pixel values in the combined image; and/or
determining the amount of tissue of each of the in plural density ranges comprises processing volumetric data (such as CT data or MRI data) for the tissue region.

In some embodiments determining the amount (e.g. thickness) of tissue of each of the in plural density ranges comprises processing the CT data to classify voxels of the CT data into the plural density ranges based on densities indicated by the CT data for the voxels, generating a volumetric mask for each of the plural density ranges, each volumetric mask comprising data indicating for voxels of the volumetric mask whether the voxel does or does not correspond to tissue of the corresponding density range, and processing the volumetric masks. In some embodiments the masks are binary masks. In some embodiments the masks have set values for voxels outside of the corresponding density range and density values for voxels belonging to the corresponding density range. In some embodiments processing the volumetric masks comprises computing digitally reconstructed radiographs (DRRs) for each of the masks from the point of view of the first and second images. Processing the volumetric masks may be based on a geometry of the first and second radiation beams and comprises determining the thickness of tissue of each of the at least two classes along rays of the first and second radiation beams corresponding to pixels of the first and second images.

In some embodiments the method comprises: identifying a region of interest and determining the weighting factors comprises:
for pixels within the region of interest selecting the weighting factors that cause increased contrast for a first selected tissue type; and for pixels outside of the region of interest selecting the weighting factors that cause de-emphasis for a second selected tissue type; and/or
for pixels within the region of interest using a first algorithm to determine the weighting factors; and for pixels outside of the region of interest using a second algorithm different from the first algorithm to determine the weighting factors; and/or.
for pixels within the region of interest selecting weighting factors from a first set of weighting factors; and for pixels outside of the region of interest selecting the weighting factors from a second set of weighting factors.

In some embodiments the first selected tissue type corresponds to soft tissue having a first density range which may, for example be a density range characteristic of tumors in the tissue region. In some embodiments the second selected tissue type corresponds to bone tissue.

Another aspect provides a method for dual energy x-ray imaging. The method comprises: using a first radiation beam acquiring a first image of a tissue region comprising at least three tissue types, each of the tissue types having a different density and using a second radiation beam acquiring a second image of the tissue region wherein an energy spectrum of the second radiation beam has a maximum energy lower than a maximum energy of an energy spectrum of the first radiation beam; and combining the first and second images to generate a combined image by determining a plurality of weighting factors and combining the first and second images using the weighting factors. The weighting factors are configured to increase contrast in the combined image of a first one of the at least three tissue types relative to others of the at least three tissue types and to deemphasize a second one of the at least three tissue types relative to others of the at least three tissue types. In some embodiments the first one of the at least three tissue types corresponds to tumor tissue.

Any of the methods described herein may optionally be applied to display and/or store and/or process the combined image and/or by processing the combined image to locate a target tissue; and to generate instructions for controlling emission of a radiation beam toward a patient based on the determined location of the target tissue.

Another aspect of the invention provides a non-transitory computer readable medium having encoded thereon machine-executable instructions that, when executed by a data processor cause the data processor to execute any of the methods as described herein.

Another aspect of the invention provides a dual energy x-ray imaging system comprising: a radiation source; an imaging radiation detector; and a processor configured to execute any of the methods described herein.

Another aspect of the invention provides a dual energy x-ray imaging system comprising: a radiation source; an imaging radiation detector; and a processor configured to control the radiation source and radiation detector to acquire plural images of a tissue region by: configuring the radiation source to emit a first radiation beam having a first energy spectrum and controlling the radiation detector to generate a first image of the tissue region corresponding to the first radiation beam passing through the tissue region and configuring the radiation source to emit a second radiation beam having second energy spectrum and controlling the radiation detector to generate a second image of the tissue region corresponding to the second radiation beam passing through the tissue region wherein a maximum energy of the second energy spectrum is lower than a maximum energy of the first energy spectrum; and combine the first and second images to generate a combined image by: separately for each of multiple parts of the first and second images, determining a corresponding weighting factor and pixelwise combining the first and second images using the weighting factors.

Another aspect of the invention provides a dual-energy x-ray imaging system comprising: an x-ray imaging device comprising a radiation source and a radiation detector; an image acquisition module, the image acquisition module configured to generate instructions instructing the x-ray imaging device to acquire a first image of a tissue region using a first radiation beam having a first energy range and to acquire a second image of the tissue region using a second radiation beam having a second energy range, the second energy range lower than the first energy range; an imaged tissue thickness computation module, the image tissue thickness module configured to compute a thickness of tissue of each of at least two classes corresponding to each of multiple parts of the first and second images; a weighting factor selection module, the weighting factor selection module configured to determine one or more weighting factors based at least in part on the thicknesses of tissue of each of at least two classes; and a dual energy image generation module, the dual energy image generation module configured to combine the first and second images to generate a combined image by, separately for each of the multiple parts of the first and second images pixelwise combining the first and second images using the determined one or more weighting factors.

Another aspect of the invention provides a radiation therapy system comprising: a radiation delivery device controllable to emit a radiation beam toward a patient; and a processor configured to obtain at least one dual energy image of a tissue region comprising a target tissue, process the at least one dual energy image to locate boundaries of the target tissue and generate instructions to control the radiation delivery device. The system is configured to generate the at least one dual energy image by a method as described herein.

Further aspects and example embodiments are illustrated in the accompanying drawings and/or described in the following description.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIG. 6A illustrates a conventional clinical single energy x-ray image of a subject's thorax. FIG. 6B illustrates a conventional dual energy x-ray image of a subject's thorax with rib bone de-emphasized. FIG. 6C illustrates a conventional dual energy x-ray image of a subject's thorax with spinal bone de-emphasized. FIG. 6D illustrates a dual energy x-ray image of a subject's thorax with both rib and spinal bone de-emphasized generated according to the methods described herein.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Figure 1:
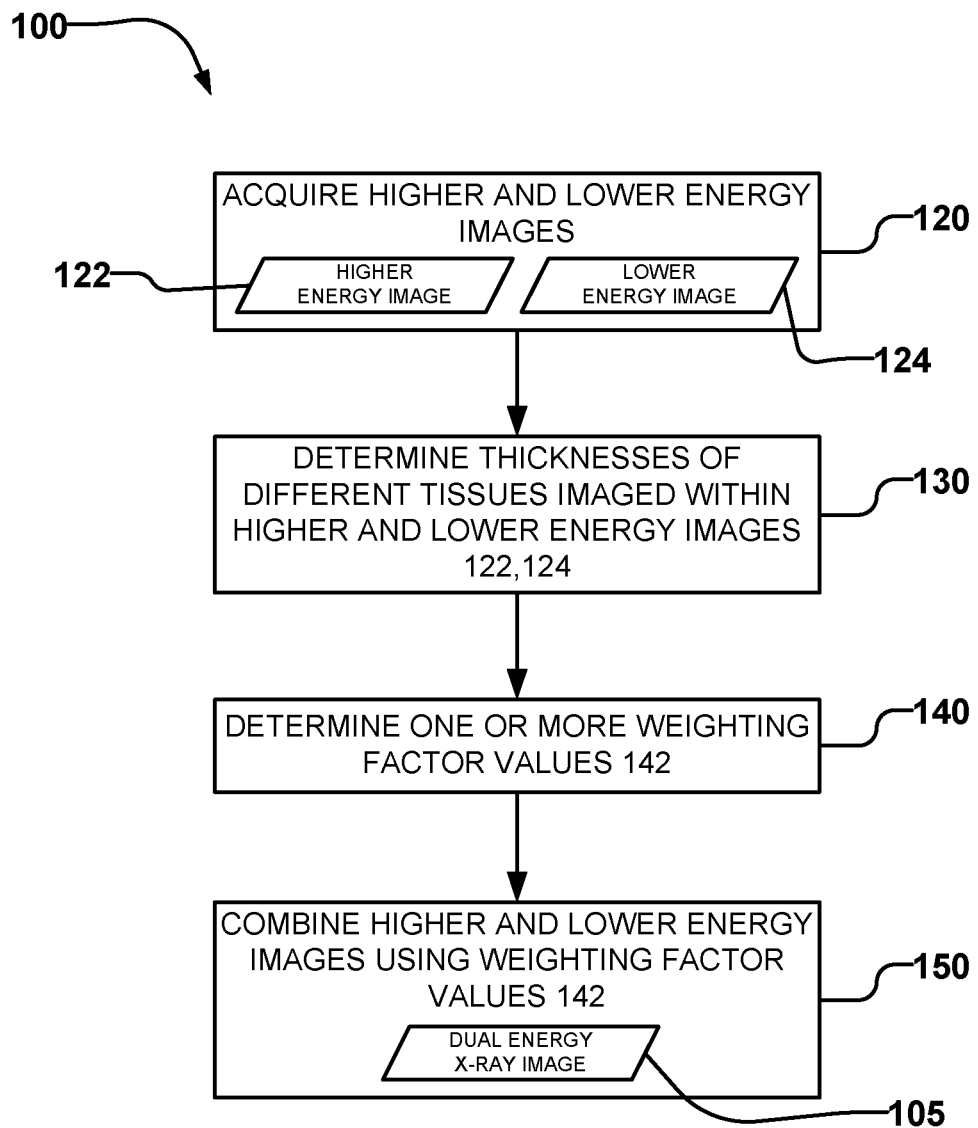
FIG. 1 is a flow chart illustrating a method according to an example embodiment.

FIG. 1 is a flow chart which illustrates at a high level an example method 100 for generating a dual energy x-ray image 105. In block 120, higher energy image 122 and lower energy image 124 corresponding to a tissue region 110 of a patient P are acquired. Tissue region 110 may, for example, correspond to patient P's thorax, abdominal region, pelvic region or the like. Tissue region 110 may, for example, include one or more bone tissue regions (e.g. ribs, vertebrae or the like) and/or one or more soft tissue regions (e.g. organ tissue (such as lung tissue, heart tissue, or the like), muscle tissue, nervous tissue, target tissue (e.g. a lung tumor or the like)).

Method 100 determines different weighting factor values for use in combining different regions of the higher and lower energy images 122, 124 based on the amounts of two or more tissue types present along paths taken by rays of higher and lower energy x-ray radiation beams responsible for imaging the regions of the images. In preferred embodiments weighting factors are selected on a pixel-by-pixel (or "pixelwise") basis.

In block 130, thicknesses of one or more tissue types (e.g. thicknesses of bone tissue, soft tissue, lung tissue, ribs, etc.) imaged within one or more pixels of higher and lower energy images 122, 124 are determined. In block 140, one or more weighting factor values 142 to be used to combine corresponding regions of higher and lower energy images 122, 124 are determined. The weighting factor values may be selected for example to emphasize and/or de-emphasize one or more tissue types (e.g. bone tissue, soft tissue, lung tissue, ribs, etc.) and/or to adjust contrast between different tissue types (e.g. tumor vs. other soft tissue) imaged within one or more pixels of higher and lower energy images 122, 124. The weighting factors may be determined based at least in part on the tissue thicknesses determined in block 130.

In block 150, higher and lower energy images 122, 124 are combined using weighting factor values 142 to generate dual energy image 105. In some embodiments, dual energy image 105 is a soft-tissue-only image of tissue region 110 (e.g. an image of patient P's thorax in which the effect of rib and/or spinal bone tissue is strongly de-emphasized). In some embodiments, dual energy image 105 is a bone-tissue-only image of tissue region 110 (e.g. an image of patient P's thorax in which the effect of lung tissue and/or other soft tissue is strongly de-emphasized).

Higher and lower energy images 122, 124 may be acquired, for example, by generating higher energy x-ray radiation beam 112 and lower energy x-ray radiation beam 114 respectively, passing beams 112,114 through tissue region 110 of patient P and detecting radiation from each of beams 112, 114 that has passed through patient P.

Higher energy radiation beam 112 may, for example, be generated using a peak x-ray tube voltage of at least 80 kVp. In some embodiments, higher energy radiation beam 112 is generated using a peak x-ray tube voltage of 140 kVp. Lower energy radiation beam 114 may, for example, be generated using a peak x-ray tube voltage below 100 kVp. In some embodiments, lower energy radiation beam 114 is generated using a peak x-ray tube voltage of 60 kVp. Peak x-ray tube voltages of at least 30 kVp are typically used. Peak x-ray tube voltages typically do not exceed 160 kVp.

In some embodiments, one or more of higher and lower energy radiation beams 112, 114 is filtered. Filtering radiation beams 112 and/or 114 may, for example, modify one or more energy spectra corresponding to radiation beams 112 and/or 114. In some embodiments, a filter applied to higher energy radiation beam 112 hardens higher energy radiation beam 112 (i.e. attenuates lower energies in an energy spectrum corresponding to radiation beam 112). In some embodiments, a filter applied to lower energy radiation beam 114 softens the lower energy radiation beam 114 (i.e. attenuates higher energies in an energy spectrum corresponding to radiation beam 114). In some embodiments a method of k-edge filtering is applied to radiation beam 114. A filter may, for example, comprise a material of a sufficient thickness and elemental composition to produce the desired filtration effect. In some embodiments, a filter is made of materials such as, lead, tin, copper, aluminum or the like.

Figure 3:
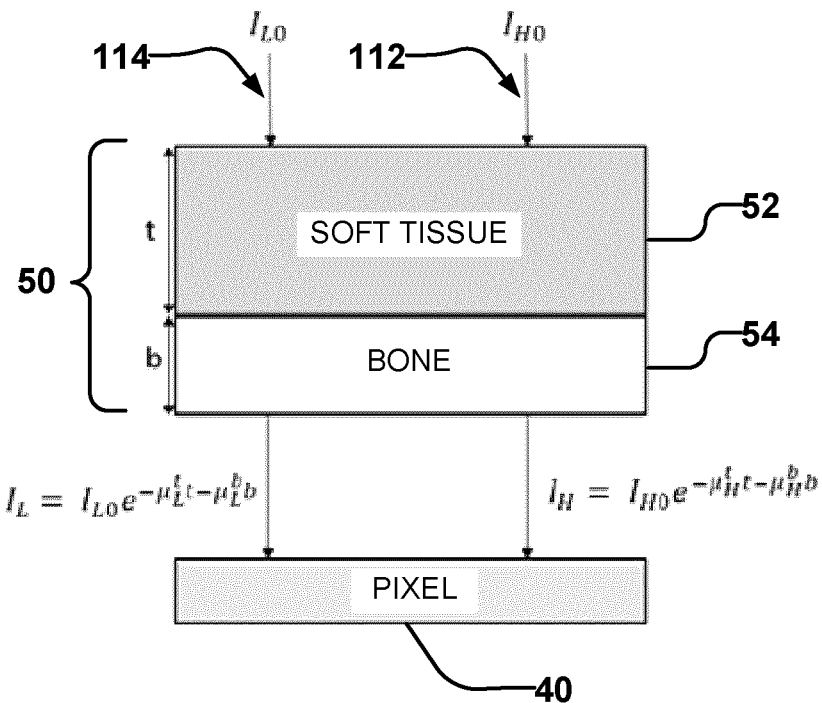
FIG. 3 is a schematic illustration showing an example imaged tissue region.
Figure 3A:
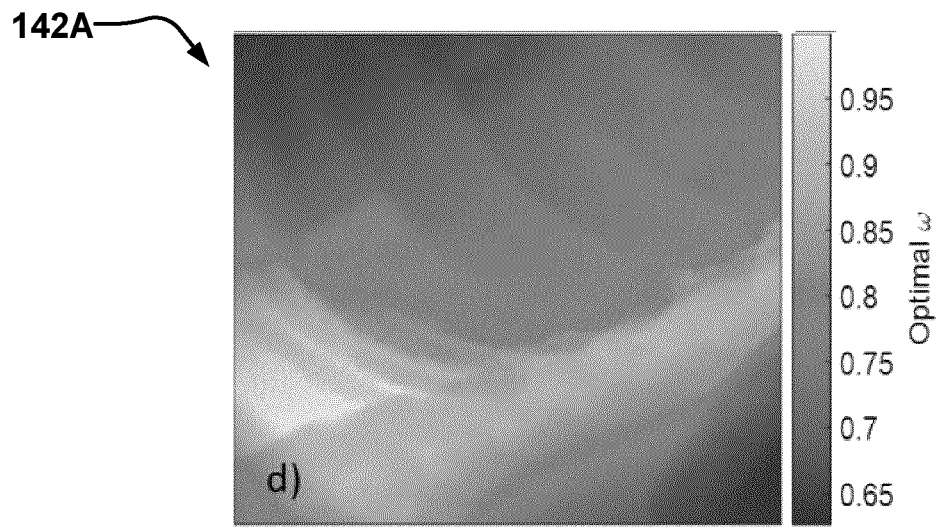
FIG. 3A illustrates an example image of weighting factor values generated according to methods as described herein.
Figure 3B:
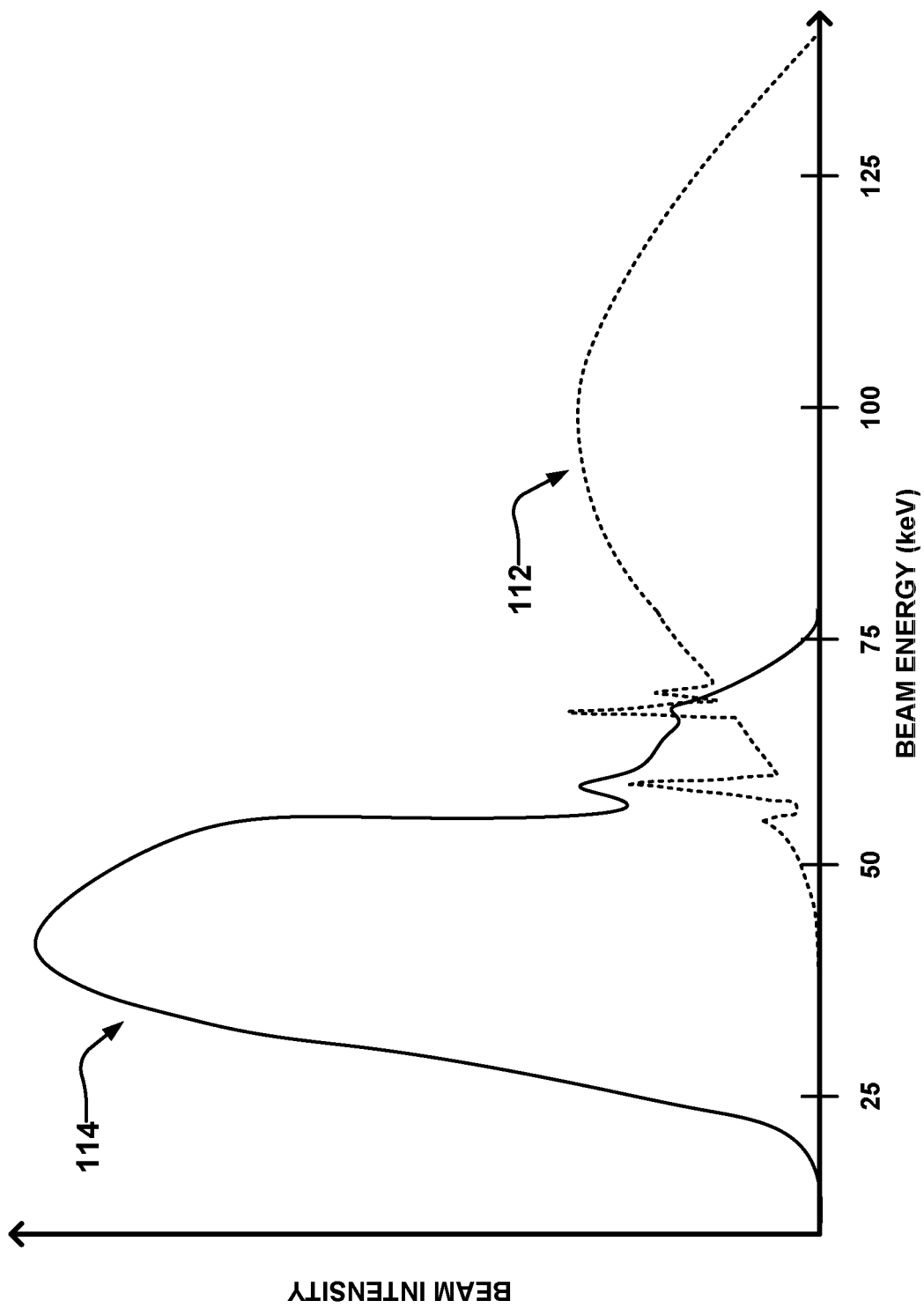
FIG. 3B shows example energy spectra for lower energy (LE) and higher energy (HE) x-ray beams.

FIG. 3B shows example energy spectra for lower energy (LE) and higher energy (HE) x-ray beams.

In some embodiments a higher quality image 105 is generated using a plurality of filters. For example, radiation beams 112 and/or 114 may each be filtered using two or more different filters that are combined (e.g. laminated, layered, etc.). In one such example embodiment:

higher energy radiation beam 112 (e.g. having a peak voltage of about 140 kVp) is filtered using an aluminum filter in combination with a 2 mm copper filter (the aluminum filter may be thicker than the copper filter. For example, the aluminum filter may have a thickness of 4 mm and the copper filter may have a thickness of 2 mm);

lower energy radiation beam 114 (e.g. having a peak voltage of about 75 kVp) is filtered using an aluminum filter in combination with a holmium filter (the aluminum filter may be thicker than the holmium filter. For example, the aluminum filter may have a thickness of 2 mm and the holmium filter may have a thickness of 0.1 mm).

In some embodiments, total x-ray dosages for acquiring higher and lower energy images 122, 124 are chosen to not exceed dosages of conventional clinical imaging protocols. In some embodiments, dosage values may be split unequally between higher and lower energy images 122, 124. In some embodiments higher dosage is allocated to the higher energy radiation beam 112. For example, 70% of a total dosage may be allocated to acquiring higher energy images 122 while the remaining 30% may be allocated to acquiring lower energy images 124.

Higher and lower energy images 122, 124 comprise m×n pixels. The number of pixels (m, n) may correspond to the number of pixels in a detector or a region of the detector used to detect radiation beams 112, 114 (e.g. detector 530 described elsewhere herein). The number of pixels (m, n) is sufficient to produce images with a desired resolution. For example, images 122, 124 may comprise 512 or more pixels in each dimension. In some embodiments, the number of pixels m is equal to the number of pixels n (e.g. 1048 in each dimension resulting in a total pixel resolution of 1048× 1048).

Higher and lower energy images 122, 124 may be acquired in any order. In some embodiments, higher energy image 122 is acquired prior to acquiring lower energy image 124. In some embodiments, lower energy image 124 is acquired prior to acquiring higher energy image 122. In preferred embodiments, a time period between acquiring higher and lower energy images 122, 124 is minimized. In such embodiments, any effects of movement of patient P on images 122, 124 may be minimized (e.g. the same tissue region 110 may be imaged in both of images 122, 124 and 1:1 spatial pixel correspondence between images 122, 124 may be achieved).

In some embodiments, one or both of higher and lower energy beams 112, 114 is presented as a plurality of fractions (i.e. lower dose x-ray radiation beams). In such embodiments, a plurality of lower dose x-ray radiation higher and/or lower energy images 122, 124 are acquired. A plurality of lower dose higher energy images 122 may be combined (e.g. by addition) to generate one higher energy image 122. Likewise, a plurality of lower dose lower energy images 124 may be combined (e.g. by addition) to generate one lower energy image 124. Breaking beams 112 and/or 114 into separate fractions can advantageously reduce the likelihood of a detector (e.g. detector 530 described elsewhere herein) entering a saturated state.

Two or more acquired images of an imaged tissue region 110 may be misaligned relative to one another. There are various reasons why a pixel (i, J) in one image may not correspond precisely to the pixel (i, J) in another image. These reasons include:

- motion of the patient (e.g. chest motion from breathing, movement of one or more limbs, etc.) during or between acquisition of the images;
- different beam geometries for the different images;
- different detectors used for the different images;
- etc.

Additionally, or alternatively, acquired images of an imaged tissue region 110 (e.g. images 122, 124) may be misaligned from two-dimensional data representative of tissue region 110 (e.g. a DRR generated from volumetric data such as CT data as described elsewhere herein, two-dimensional images generated from three dimensional data representative of tissue region 110, etc.). There are various reasons why a pixel (i, J) in the acquired images may not correspond precisely to the two-dimensional data representative of the pixel (i, J). These reasons may include one or more of the reasons described above. These reasons may also include:

- different imaging modalities used to acquire the images of the tissue region and the data representative of the tissue region;
- different positioning and/or posture of the patient (e.g. patient geometries) for acquiring images of the tissue region and data representative of the tissue region;
- different spatial resolution of the acquired x-ray images and data;
- tumor shrinkage or growth (e.g. may displace tissue, etc.); etc.

Such misalignments may be corrected by applying a transformation to one or both images. Applying a transformation to cause pixelwise alignment of the images may be called "registration". In some embodiments registration involves transformations which provide one or more of:

- rigid displacements in one or more directions;
- rigid rotations;
- scaling;
- non-rigid and/or deformable local (e.g. different variable transformations may be applied to different regions of an image) stretching, displacement and/or rotation.

By applying a transformation, acquired images of a tissue region 110 may be registered together. Preferably, images that are to be combined are registered together prior to combining the images. Preferably, images of the tissue region are registered with two dimensional data representative of the tissue region generated from three-dimensional volumetric imaging as described elsewhere herein (e.g. to correct for misalignment between acquired images of the tissue region and data representative of the tissue region as described above).

As described elsewhere herein, an imaged tissue region 110 may comprise several different tissues having different densities. For the purposes of the technology described herein, tissue density corresponds to tissue properties which vary a degree to which x-rays are attenuated when they pass through the tissue. Denser tissues attenuate x-ray beams more strongly than tissues that have lower density. Tissue density may, for example, depend on atomic numbers of elements in the tissue as well as the mass density of the tissue. These factors can depend in turn on factors such as the nature of cell structures contained within the tissue (e.g. what type of cell(s) form the tissue), cell organization within the tissue (e.g. whether the cells forming the tissue are organized close together or sparsely within the tissue) or the like. For example, bone tissue 54 has a higher density than soft tissue 52.

Figure 2:
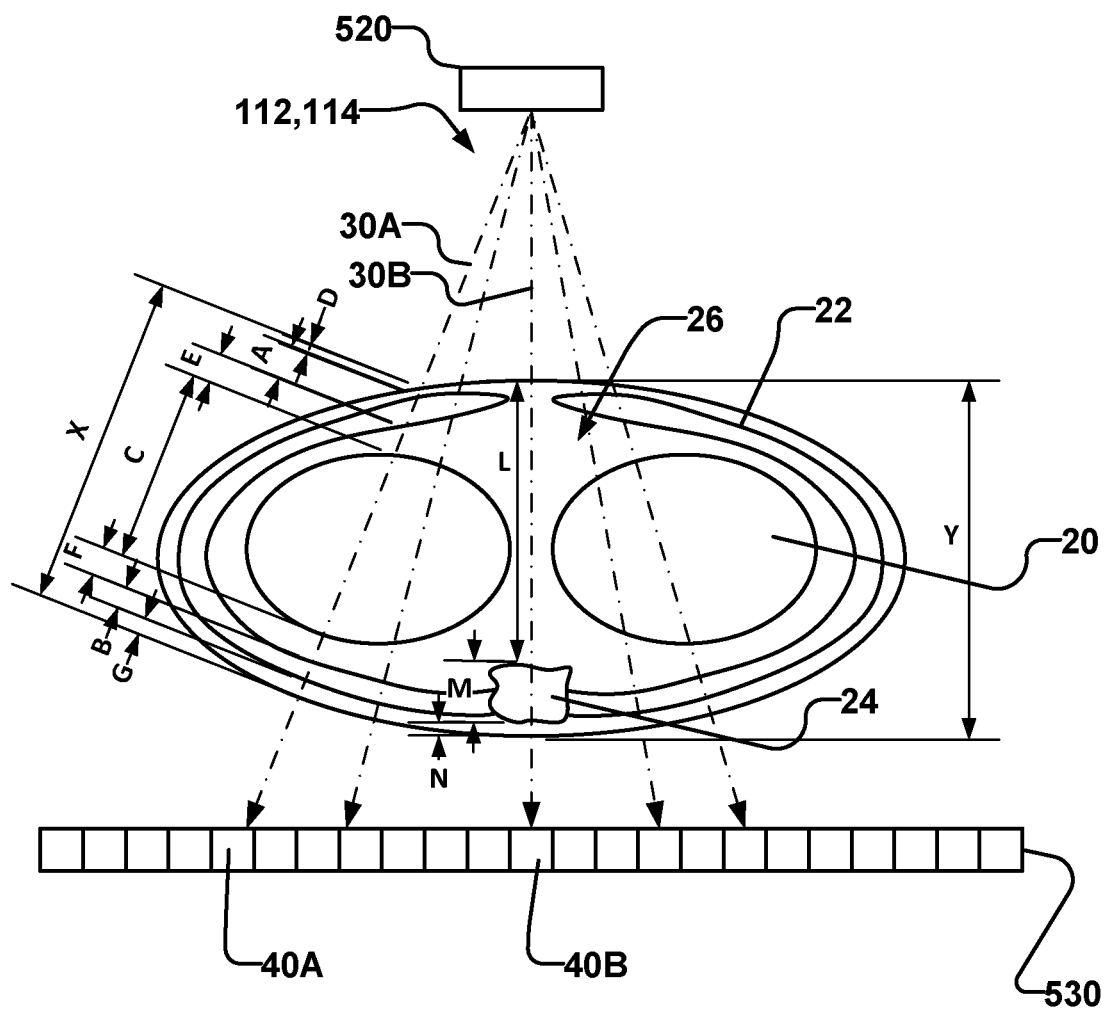
FIG. 2 is a schematic illustration showing an example imaged tissue region of a subject.

The makeup of tissue corresponding to a pixel of higher and lower energy images 122, 124 (i.e. tissues lying along a line extending from an x-ray source to a pixel of an x-ray detector) may vary on a pixel-by-pixel basis. Total thicknesses of different tissue types (e.g. of each tissue having a different density) corresponding to a pixel of higher and lower energy images 122, 124 may vary on a pixel-by-pixel basis. For example, where tissue region 110 corresponds to patient P's thorax, tissue region 110 may comprise lung tissue 20, ribs 22, vertebrae 24 and soft tissue other than lung tissue 26 as shown in FIG. 2.

An x-ray 30A (e.g. a sample ray of radiation beam 112 or 114 emitted from radiation source 520) corresponding to pixel 40A (e.g. a sample pixel of higher or lower energy image 122, 124 of a detector 530) passes through tissue having a total thickness X. Total tissue thickness X comprises rib bone thicknesses A and B, lung tissue thickness C and other soft tissue thicknesses D, E, F and G. X-ray 30B corresponding to pixel 40B passes through tissue having a total thickness Y. Total tissue thickness Y comprises vertebrae thickness M and remaining soft tissue thicknesses L and N. Total tissue thickness Y may be different from, or the same as, total tissue thickness X.

In some embodiments, different tissue types (e.g. tissues having different densities) corresponding to a pixel of images 122, 124 may be classified into two or more classes. For example, soft tissue 52 may be assigned to one class and bone tissue 54 may be assigned to a second class. For example, lung tissue 20 and soft tissue other than lung tissue 26 may be classified generally as soft tissue 52. Ribs 22 and vertebrae 24 may, for example, be classified generally as bone tissue 54.

Classification of tissue into different types may be based on tissue density. The tissue density at different locations within a tissue region 110 may, for example, be determined by way of a CT scan or other imaging modality that detects tissue characteristics related to tissue density. Additionally, or alternatively, the tissue density at different locations may be determined by way of generated two-dimensional images corresponding to the CT scan or other imaging modality data (e.g. a DRR as described elsewhere herein).

In some embodiments the tissue density is determined directly from higher and lower energy images 122, 124 as described elsewhere herein. Advantageously, in such embodiments the CT or other imaging modality data is not required (e.g. reduces patient exposure to radiation, reduces how many imaging procedures a patient may have to undergo, etc.).

In embodiments where tissue 50 corresponding to a pixel 40 of higher and lower energy images 122, 124 is classified by density into two classes, the tissue 50 may be modeled as shown in FIG. 3. Tissue 50 comprises soft tissue 52 having a total thickness t along an x-ray and bone tissue 54 having a total thickness b along the x-ray. Values of pixel 40 in higher and lower energy images 122, 124 corresponding to imaged tissue 50 may respectively be represented as:

$$I_{HE} = I_{HO} e^{-\mu_H^t t - \mu_H^b b} \qquad (1)$$

$$I_{LE} = I_{LO} e^{-\mu_L^t t - \mu_L^b b} \qquad (2)$$

where $I_{HO}$, $I_{LO}$ are respectively the intensities of higher and lower energy radiation beams 112, 114 incident on tissue 50, $I_{HE}$ and $I_{LE}$ are the detected intensities of beams 112, 114 respectively upon passing through tissue region 50, $\mu_H^t$ and $\mu_L^t$ are the linear attenuation coefficients for soft tissue 52 for higher and lower energy radiation beams 112, 114 respectively, $\mu_H^b$ and $\mu_L^b$ are the linear attenuation coefficients for bone tissue 54 for higher and lower energy radiation beams 112, 114 respectively, and t and b are respectively the soft tissue 52 and bone tissue 54 thicknesses as defined above.

Equations (1) and (2) may be converted to linear equations by computing the logarithm, for example the natural logarithm (i.e. ln( )) of each of Equations (1) and (2). Linearizing Equations (1) and (2) may simplify combining of higher and lower energy images 122, 124 to generate dual energy image 105 (e.g. block 150 of method 100).

The fact that the linear attenuation coefficients for a given tissue type are generally different for higher and lower energy radiation beams 112, 114 may be used to find a computational combination of higher and lower energy images 122, 124 in which a selected tissue type is emphasized or de-emphasized. The technology described herein determines such combinations on a pixel-by-pixel basis (or separately for small regions that may be larger than a pixel).

The combination of images 122, 124 may apply one or more weighting factor values 142 to pixels (or small regions) of higher and/or lower energy images 122, 124 to selectively emphasize or de-emphasize one or more tissue types in corresponding pixels of the resulting dual energy image 105 (e.g. block 140 of method 100).

For example, weighting factor values 142 may be selected to de-emphasize bone tissue 54 (i.e. emphasizing soft tissue 52) or to de-emphasize soft tissue 52 (i.e. emphasizing bone tissue 54). In some embodiments, weighting factor values 142 may be selected to de-emphasize more specific tissue types such as, for example, lung tissue, ribs, muscle tissue, or the like. In some embodiments weighting factor values 142 may be chosen to enhance the contrast of a particular tissue type with tissues of other types (for example, to enhance the contrast in dual energy image 105 between a tumor and normal tissues near the tumor).

In some embodiments, higher and lower energy images 122, 124 may be combined using weighting factor values 142 optimized to de-emphasize bone tissue 54 to generate a soft-tissue-only dual energy image 105. The combination may be a linear combination. For example, in some embodiments, a soft-tissue-only dual energy image 105 is generated by subtracting lower energy image 124 from higher energy image 122 in combination with applying weighting factor values 142 optimized to de-emphasize bone tissue 54 to one or both of higher and lower energy images 122, 124.

In some embodiments, a soft-tissue-only dual energy image 105 is generated as follows:

$$\ln(I_{DE_T}) = \ln(I_{HE}) - \omega_T \ln(I_{LE}) \qquad (3)$$

where $I_{DE_T}$ represents pixel intensities of the generated dual energy soft-tissue-only image 105, $I_{HE}$ represents pixel intensities of higher energy image 122, $\omega_T$ represents weighting factor values 142 optimized for de-emphasizing of bone tissue 54 and $I_{LE}$ represents pixel intensities of lower energy image 124.

In some embodiments, higher and lower energy images 122, 124 and weighting factor values 142 optimized to de-emphasize soft tissue 52 may be combined to generate a bone-tissue-only dual energy image 105. The combination may be linear. For example, in some embodiments, a bone-tissue-only dual energy image 105 is generated by subtracting higher energy image 124 from lower energy image 122 in combination with applying weighting factor values 142 optimized to de-emphasize soft tissue 52 to one or both of higher and lower energy images 122, 124.

In some embodiments, a bone-tissue-only dual energy image 105 is generated as follows:

$$\ln(I_{DE_B}) = -\ln(I_{HE}) + \omega_B \ln(I_{LE}) \qquad (4)$$

where $I_{DE_B}$ represents pixel intensities of the generated dual energy bone-tissue-only image 105, $I_{HE}$ represent pixel intensities of higher energy image 122, $\omega_B$ represents optimal pixel-specific weighting factor values 142 optimized for de-emphasizing of soft tissue 52 and $I_{LE}$ represents pixel intensities of lower energy image 124.

In some embodiments higher and lower energy images 122, 124 and weighting factor values 142 optimized to enhance contrast between two soft tissue types may be combined to generate an enhanced contrast image. The combination may be linear. For example, in some embodiments, an enhanced contrast dual energy image 105 is generated by subtracting lower energy image 124 from higher energy image 122 in combination with applying weighting factor values 142 optimized to enhance contrast between tumor tissues and other tissues.

In some embodiments, an enhanced contrast dual energy image 105 is generated as follows:

$$\ln(I_{DE_{Tmax}}) = \ln(I_{HE}) - \omega_{Tmax} \ln(I_{LE}) \qquad (5)$$

where $I_{DE_{Tmax}}$ represents pixel intensities of the generated dual energy enhanced contrast image 105, $I_{HE}$ represents pixel intensities of higher energy image 122, $\omega_{Tmax}$ represents weighting factor values 142 optimized for enhancing contrast of tumor tissue and $I_{LE}$ represents pixel intensities of lower energy image 124.

In some embodiments, weighting factor values 142 are applied to higher energy image 122 or to both higher energy image 122 and lower energy image 124 to generate dual energy image 105.

In some embodiments dual energy image 105 is generated by a pixelwise weighted subtraction of a function of higher energy image 122 and a function of lower energy image 124. Weighting may be provided by one or more weighting factor values 142 applied to one or both of the function of higher energy image 122 and the function of lower energy image 124.

In some embodiments, a weighting factor value 142 is separately determined for each pixel of higher or lower energy images 122, 124. In some embodiments, a different weighting factor value 142 is applied to different pixel regions (i.e. a region comprising one or more pixels) of higher or lower energy images 122, 124. In some embodiments, weighting factor values 142 de-emphasize different tissue types in different pixel regions of dual energy image 105.

A weighting factor value 142 may, for example, be determined based on thicknesses of different tissue types corresponding to a pixel of higher or lower energy images 122, 124. In some embodiments, a weighting factor value 142 is determined by using thicknesses of different tissue types corresponding to a pixel to, for example, calculate a weighting factor value 142, retrieve a weighting factor value 142 from memory, interpolate and/or extrapolate a weighting factor value 142 or the like. In some embodiments, a ratio of thicknesses of different tissue types corresponding to a pixel is used to determine a weighting factor value 142.

Weighting factor values 142 may be represented in a data structure that provides a weighting factor for each pixel (a weighting factor image). The weighting factor image may have the same or different resolution as the lower and higher energy images 122, 124. The weighting factor image is preferably registered with the lower and higher energy images 122, 124 so that the correct weighting factor(s) for a pixel (i,j) can be readily determined. If the weighting factor image is not registered to the lower and higher energy images 122, 124 then a registration step may apply a transformation as described above to achieve registration of the weighting factor image with lower and higher energy images 122, 124. To facilitate registration it can be desirable to make the weighting factor image larger than the lower and higher energy images 122, 124 (e.g. by including a margin around the weighting factor image) so that translations, rotations scaling etc. of the weighting factor image relative to lower and higher energy images 122, 124 within ranges required to achieve registration do not cause pixels of lower and higher energy images 122, 124 to fall outside of the registration image (i.e. to avoid losing edges of the weighting factor image as a result of registration).

FIG. 3A illustrates an example weighting factor image 142A generated to de-emphasize bone tissue 54 from tissue region 110 corresponding to patient P's thorax. The weighting factor image shows how optimal weighting factors vary for different pixels in the image.

Thicknesses of each different tissue type corresponding to a pixel of higher and/or lower energy images 122, 124 may be ascertained from data representative of tissue region 110 of patient P. For example, such data may comprise MRI images or CT images of tissue region 110, data corresponding to tissue region 110 stored in memory, data provided by a user or the like. Such data may be acquired before or after acquiring higher and/or lower energy images 122, 124. In some embodiments, computed tomography images (CT images) of tissue region 110 are processed to determine thicknesses of tissue of different types in a tissue region of a patient from the point of view of desired higher and/or lower energy images 122, 124. In some embodiments the thicknesses are determined for each pixel of the higher and/or lower energy images 122, 124

Data representative of tissue region 110 may be processed to ascertain thicknesses of different tissue types corresponding to pixels or other areas of higher and/or lower energy images 122, 124. There are a wide range of ways in which this can be done. By way of non-limiting example:

The paths of rays corresponding to pixels may be traced, the densities of tissues along the rays may be ascertained from the data and the total thickness of tissues of plural density ranges may be totaled for each ray. This process may itself be done in various ways including:

Determining densities or density ranges for voxels lying in planes through which the rays pass and locating the voxel in each plane through which each ray passes;

Determining densities or density ranges for voxels lying in planes in which the rays lie, tracing the path of each ray in a corresponding plane and totaling the thicknesses of tissues for plural density ranges along each ray;

Using digitally reconstructed radiographs, for example, as described below.

Estimates of thickness of tissues of different types may be made from physical measurements of a patient in combination with conventional x-rays. Such estimates may be used as a basis for determining weighting factors. For example, an x-ray image may be processed to determine locations of ribs or other bones of a patient. Thicknesses of the ribs (or other tissues generally) may, for example, be estimated based on factors which may include: information about the patient such as the age, sex, body size and/or racial background of the patient; information obtained by processing the x-ray image such as width of the ribs or observed density of portions of the x-ray image corresponding to the ribs; information obtained by processing images of tissue regions comprising the ribs obtained from imaging modalities other than x-ray imaging (e.g. MRI, etc.);

Estimates of the thickness of bone and soft tissue may be obtained by processing higher and lower energy x-ray images 122, 124. Such processing may comprise decomposing each of images 122, 124 into a plurality of basis materials (e.g. soft tissue and bone tissue). "Decomposing" means that pixels of an image are binned into one of a plurality of groups corresponding to each of the basis materials. For example, as described in Li, H., W. Giles, L. Ren, J. Bowsher, and F. F. Yin. 2012. "Implementation of Dual-Energy Technique for Virtual Monochromatic and Linearly Mixed CBCTs." Medical Physics 39 (10): 6056-6064. doi: 10.1118/1.4752212, the relative thicknesses of bone b(i,j) and soft tissue t(i,j) corresponding to a pixel (i,j) may be determined by solving the following system of equations for b(i,j) and t(i,j):

$$\ln\left(\frac{I_{HE}(i,j)}{I_{HO}(i,j)}\right) = -\mu_H^t t(i,j) - \mu_H^b b(i,j) \tag{6}$$

$$\ln\left(\frac{I_{LE}(i,j)}{I_{LO}(i,j)}\right) = -\mu_L^t t(i,j) - \mu_L^b b(i,j) \tag{7}$$

to obtain:

$$\begin{bmatrix} t(i,j) \\ b(i,j) \end{bmatrix} = \begin{bmatrix} -\mu_H^t - \mu_H^b \\ -\mu_L^t - \mu_L^b \end{bmatrix}^{-1} \begin{bmatrix} \ln\left(\frac{I_{HE}(i,j)}{I_{HO}(i,j)}\right) \\ \ln\left(\frac{I_{LE}(i,j)}{I_{LO}(i,j)}\right) \end{bmatrix} \quad (8)$$

This approach has the advantage that the weighting factor image is automatically registered with lower and higher energy images 122, 124.

Processing of the data may comprise classifying the data by tissue type (e.g. each of a plurality of categories or bins may comprise data for tissues of a corresponding range of tissue densities).

Different measures of tissue thickness may be used. In some embodiments, tissue thickness for a category is measured by determining a physical length in which the data indicates tissues of a particular category (or equivalently a number of pixels or voxels for which the data indicates tissues of the particular category). In some embodiments, variations of tissue density in each category are taken into account. For example, for a soft tissue category a thickness may be determined by totaling densities (or normalized densities) indicated by the data for pixels or voxels along a particular ray or path.

In some embodiments, thicknesses of different tissue types are ascertained by processing the data directly (i.e. without a prior distinct step for classifying the data). In some embodiments, CT or other volumetric data may be processed to generate tissue thickness maps of tissue region 110. The tissue thickness maps may, for example, comprise digitally reconstructed radiographs. In some embodiments, the tissue thickness maps may be generated using existing software which provides functionality for generating digitally reconstructed radiographs.

Figure 4:
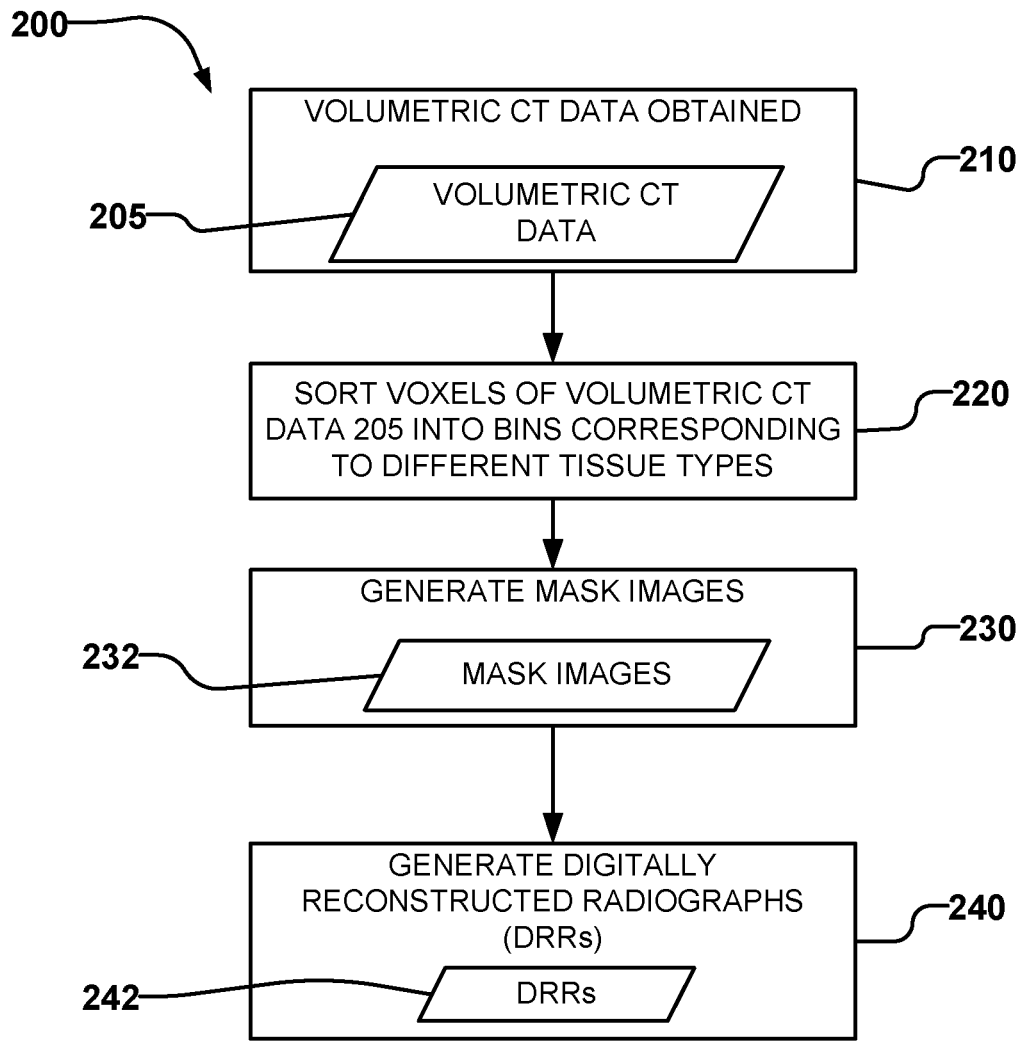
FIG. 4 is a flow chart illustrating a method according to an example embodiment.

FIG. 4 is a flow chart illustrating an example method 200 for using volumetric CT data corresponding to tissue region 110 to ascertain thicknesses of different tissue types imaged in one or more pixels of higher and/or lower energy images 122, 124. Other volumetric data such as MRI data could be processed in a similar manner.

In block 210, volumetric CT data 205 corresponding to tissue region 110 is obtained. CT data 205 may, for example, be represented as a three-dimensional matrix (e.g. a three dimensional image of tissue region 110). Each entry (i.e. a voxel) in the three-dimensional matrix, for example, corresponds to a density of tissue within tissue region 110 (e.g. a Hounsfield Unit value). In some embodiments, the three-dimensional matrix comprises and/or can be visualized as an array of two dimensional CT images representing cross-sectional slices of tissue region 110.

In block 220, voxels of the volumetric CT data 205 are sorted into bins corresponding to different tissue types. For example, the voxels may be sorted into a first bin corresponding to soft tissue 52 and a second bin corresponding to bone tissue 54. Sorting of voxels into bins may, for example, be based on a measure of density of tissue corresponding to a voxel value (e.g. a Hounsfield Unit value).

In some embodiments, voxels of the volumetric CT data 205 may, for example, be sorted into three or more bins corresponding to three or more different tissue types. For example, the voxels may be sorted into a first bin corresponding to lung tissue 20, a second bin corresponding to soft tissue other than lung tissue 26 and a third bin corresponding to bone tissue 54. In an example embodiment, Hounsfield Unit values of less than −650, between −650 and less than 250, and between 250 and less than 2000 are used to sort the voxels into bins corresponding to lung tissue 20, to soft tissue other than lung tissue 26 and to bone tissue 54 respectively. In some embodiments, Hounsfield Unit values less than −840, between −840 and less than or equal to −650, greater than −650 and less than or equal to 250, and greater than 250 are used to sort the voxels into bins corresponding to air (i.e. not tissue), to lung tissue 20, to soft tissue other than lung tissue 26 and to bone tissue 54 respectively.

In embodiments where the volumetric CT data 205 comprises an array of two dimensional CT images (i.e. an array of two dimensional cross-sectional slices of the volumetric CT data 205), pixels (as opposed to voxels) of each CT image in the array of CT images may be sorted into different bins corresponding to different tissue types as described herein. A pixel of a two dimensional CT image may, for example, be represented as a voxel where the height of the voxel corresponds to a spatial resolution thickness of tissue region 110 that the two dimensional CT image represents.

In block 230, mask images 232 are generated using the sorted voxels. Each mask image 232 corresponds to a different bin used in block 220 to sort the voxels. For example, a first mask image 232 may correspond to a first bin corresponding to soft tissue 52 and a second mask image 232 may correspond to a second bin corresponding to bone tissue 54.

Each mask image 232 comprising a plurality of voxels may, for example, be represented as a three dimensional matrix.

In some embodiments, mask images 232 are binary. In such embodiments, a first value (e.g. a value of 1) is used to indicate presence of a tissue type in a region corresponding to a voxel of volumetric CT data 205 and a second value different from the first value (e.g. a value of 0) is used to indicate an absence of the tissue type in the region corresponding to the voxel. In other embodiments mask images contain density values for voxels that correspond to a tissue type that the mask relates to and voxels that correspond to other tissue types may be set to a suitable value such as a density of air or a vacuum in the density units being used.

Figure 4A:
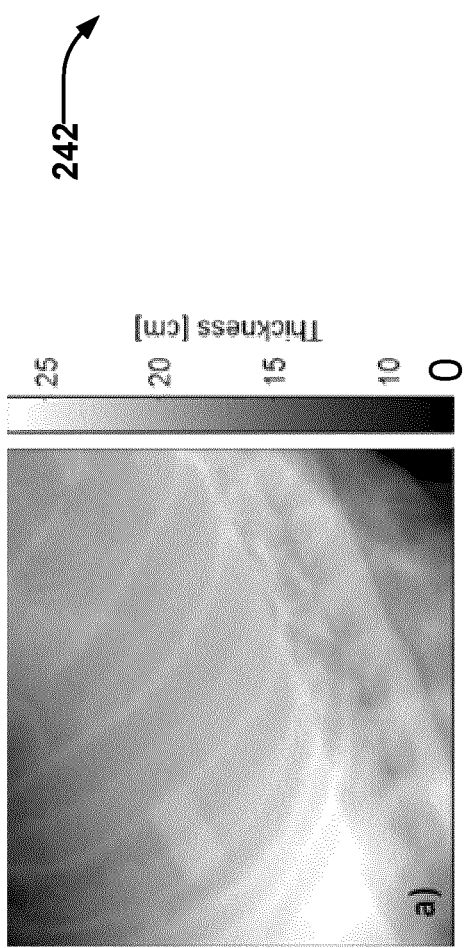
FIGS. 4A to 4C illustrate example digitally reconstructed radiographs.
Figure 4B:
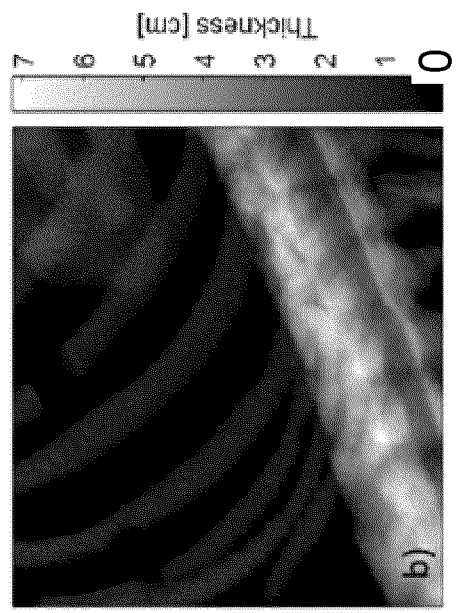
Figure 4C:
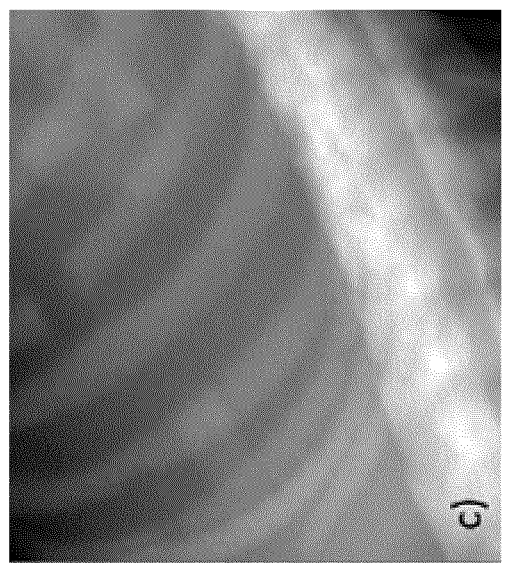

In block 240, the generated mask images 232 are used to generate different digitally reconstructed radiographs (DRRs) 242 corresponding to different tissue types. For example, a mask image 232 corresponding to a bin used to sort voxels of volumetric CT data 205 that comprise bone tissue 54 may be used to generate a DRR 242 corresponding to bone tissue 54 contained within tissue region 110. Once a DRR 242 for a tissue type is generated, each pixel value of the DRR 242 corresponds to a thickness of that tissue type. FIGS. 4A, 4B, 4C illustrate example DRRs 242 of soft tissue 52, bone tissue 54, and combined soft tissue 52 and bone tissue 54 respectively of patient P's thorax.

A DRR 242 may, for example, be generated by ray tracing through a mask image 232. For example, a tracing ray may be modeled as a 3D vector connecting a source point on a radiation source (e.g. radiation source 520 described elsewhere herein). In some embodiments, ray tracing according to Siddon's method may be used (Siddon, R. L. 1985. "Fast Calculation of the Exact Radiological Path for a Three-Dimensional CT Array." Medical Physics 12 (2): 252-255. doi:10.1118/1.595715). In some embodiments, DRRs 242 are generated using a commercially available DRR generator. In some embodiments, DRRs 242 are generated for a plane containing a selection of rays of radiation beams 112, 114. In some embodiments, DRRs 242 correspond to beam's eye view images as seen from a radiation source.

Figure 4D:
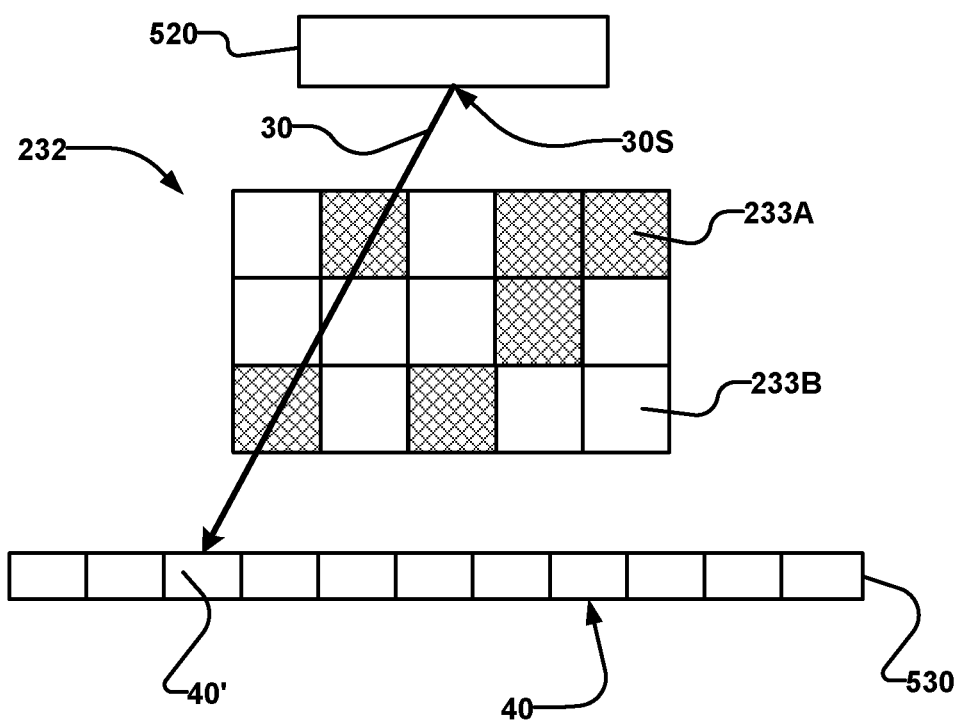
FIG. 4D is a schematic illustration showing an example ray tracing method.

FIG. 4D schematically illustrates an example ray tracing method using a generated mask image 232.

Ray 30 extending from a source point 30S of radiation source 520 to a pixel 40' of detector 530 comprising a plurality of pixels 40 passes through a plurality of voxels 233A, 233B of mask image 232. Voxels 233A correspond to voxels of volumetric CT data 205 that represent a tissue type (e.g. bone tissue 54). Voxels 233B correspond to voxels of volumetric CT data 205 that do not represent the tissue type. As shown in FIG. 4D, ray 30 passes through two voxels 233A representing a thickness of the tissue type along ray 30 to be two voxel units. Ray 30 may, for example, be used to generate a value for pixel 40' in a DRR 242 for the tissue type that corresponds to a tissue thickness of two voxel units.

In some embodiments, a generated DRR 242 of a first tissue type may be scaled by a density ratio between the first tissue type and a second different tissue type to convert a thickness of the first tissue type to an equivalent thickness of the second tissue type (e.g. when the effective atomic numbers of the first and second tissue types are similar). For example, a DRR 242 generated for lung tissue 20 thickness may be scaled by a density ratio between lung tissue 20 and soft tissue 52 to convert lung tissue 20 thickness to an equivalent soft tissue 52 thickness.

In some embodiments, generating a DRR 242 may include modeling factors specific to an x-ray imaging system. Such factors may, by way of non-limiting example, include:
- Geometries of a radiation source and/or a detector (e.g. radiation source 520 and/or detector 530 described elsewhere herein). For example, azimuth and/or elevation angles of x-ray tubes within a radiation source may be modeled.
- A radiation source to isocenter distance and/or a source to detector distance. Modeling such distances may ensure an x-ray imaging system has a correct field-of-view at its isocenter and/or on a surface of its detector.

Figure 4E:
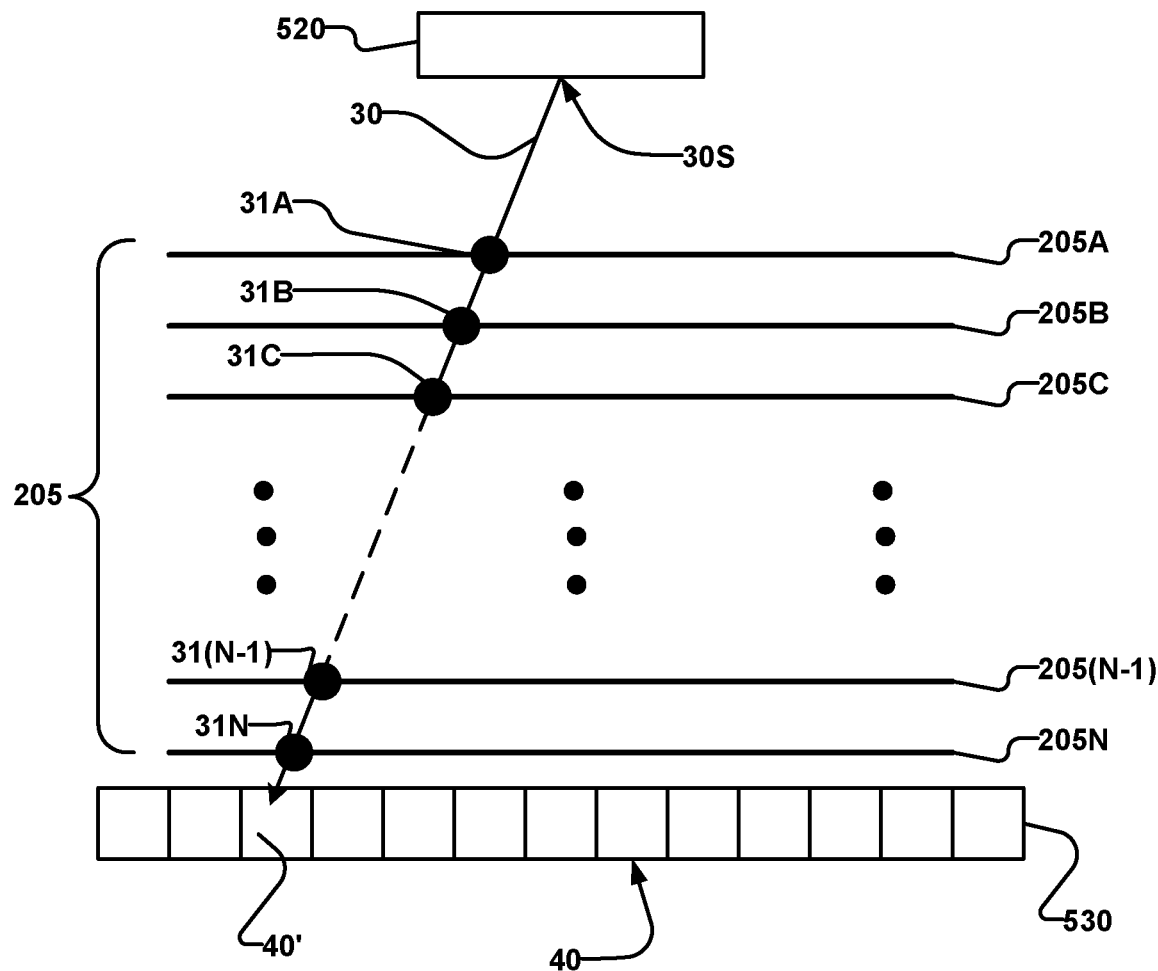
FIG. 4E is a schematic illustration showing an example ray tracing method.

In some embodiments, thicknesses of each different tissue type corresponding to a pixel of higher and/or lower energy images 122, 124 is ascertained by ray tracing through volumetric CT data 205. FIG. 4E schematically illustrates an example ray tracing method through volumetric CT data 205 comprising an array of two dimensional CT images representing cross-sectional slices of tissue region 110 (i.e. images 205A, 205B, 205C, . . . , 205(N−1), 205N).

In FIG. 4E, tracing ray 30 extends from a source point 30S of radiation source 520 to a pixel 40' of detector 530 comprising a plurality of pixels 40. Ray 30 passes through a distinct area 31 of each two dimensional CT image (i.e. regions 31A, 31B, 31C, . . . , 31(N−1), 31N). A total thickness of a tissue type may be calculated by summing the total number of areas 31 containing that tissue that tracing ray 30 passes through.

Calculated tissue thicknesses for two or more different tissue types corresponding to a pixel of higher and/or lower images 122, 124 may be used to retrieve values for weighting factor values 142 from memory and/or determine values for weighting factors by calculation using an empirically derived formula.

In some embodiments, a plurality of pre-calibrated weighting values corresponding to a plurality of different thicknesses of different tissue types is stored in memory or a suitable lookup table. For example, calculated bone tissue 54 thickness of 4 cm and soft tissue 52 thickness of 20 cm may be used as keys to look up a weighting factor value 142 for de-emphasizing bone tissue 54 which is indexed as corresponding to a bone tissue 54 thickness of 4 cm and a soft tissue 52 thickness of 20 cm. In some embodiments, the plurality of pre-calibrated weighting values corresponds to a plurality of different ratios of thicknesses of different tissue types.

Figure 5:
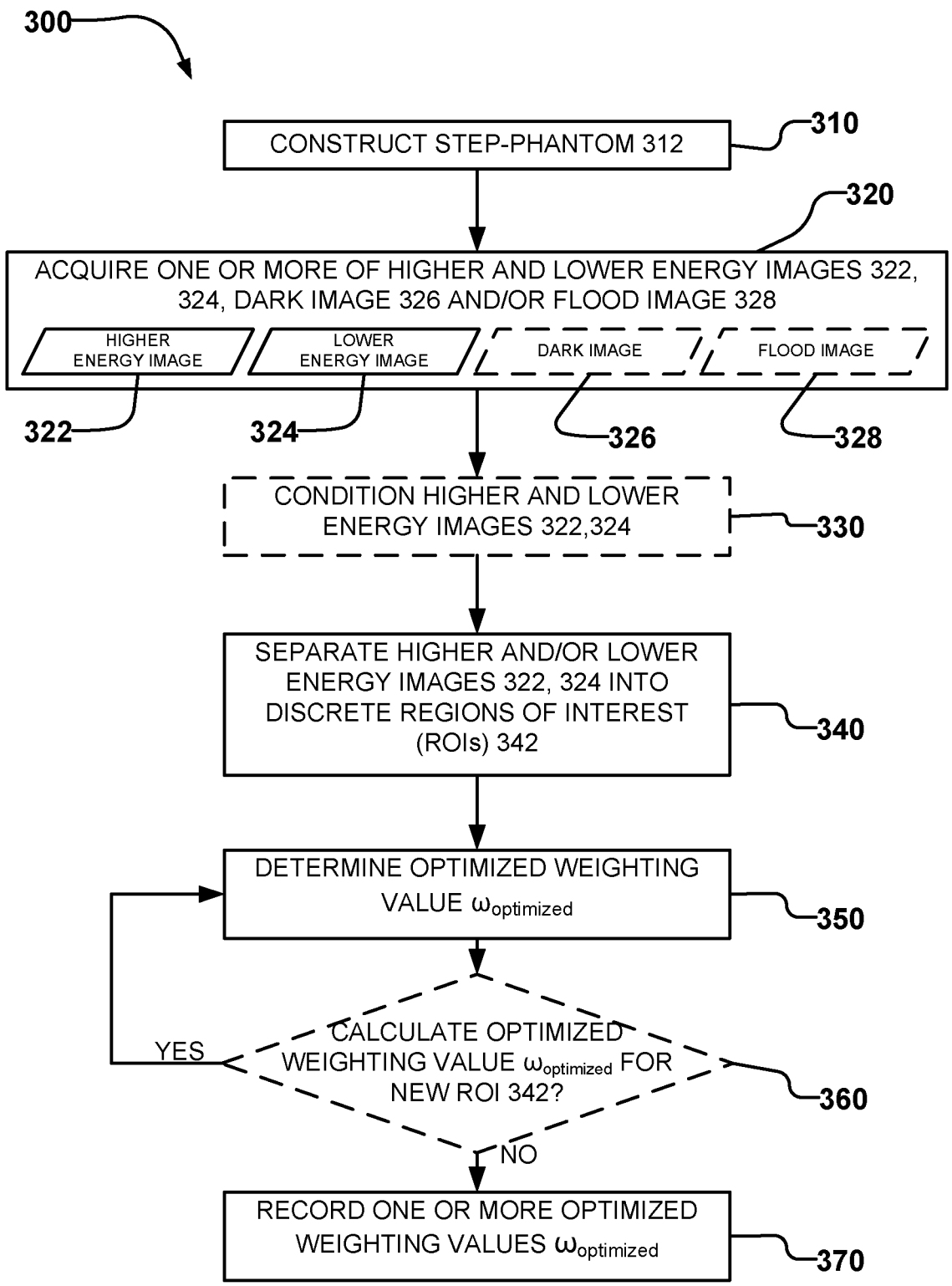
FIG. 5 is a flow chart illustrating a method according to an example embodiment.

In some embodiments, pre-calibrated weighting values may be generated by processing data collected by imaging one or more tissue models using radiation beams 112 and 114. Each model comprises one or more thicknesses of material that simulates one or more tissue types (e.g. soft tissue 52 and/or bone tissue 54). For example, the tissue model may be a step-phantom (a tissue model comprising at least two different thicknesses of each of at least two tissue types—in the step phantom the different thicknesses are arranged in a "step-like" pattern). FIG. 5 is a flow chart showing an example method 300 for generating pre-calibrated weighting values using a step-phantom 312.

Figure 5A:
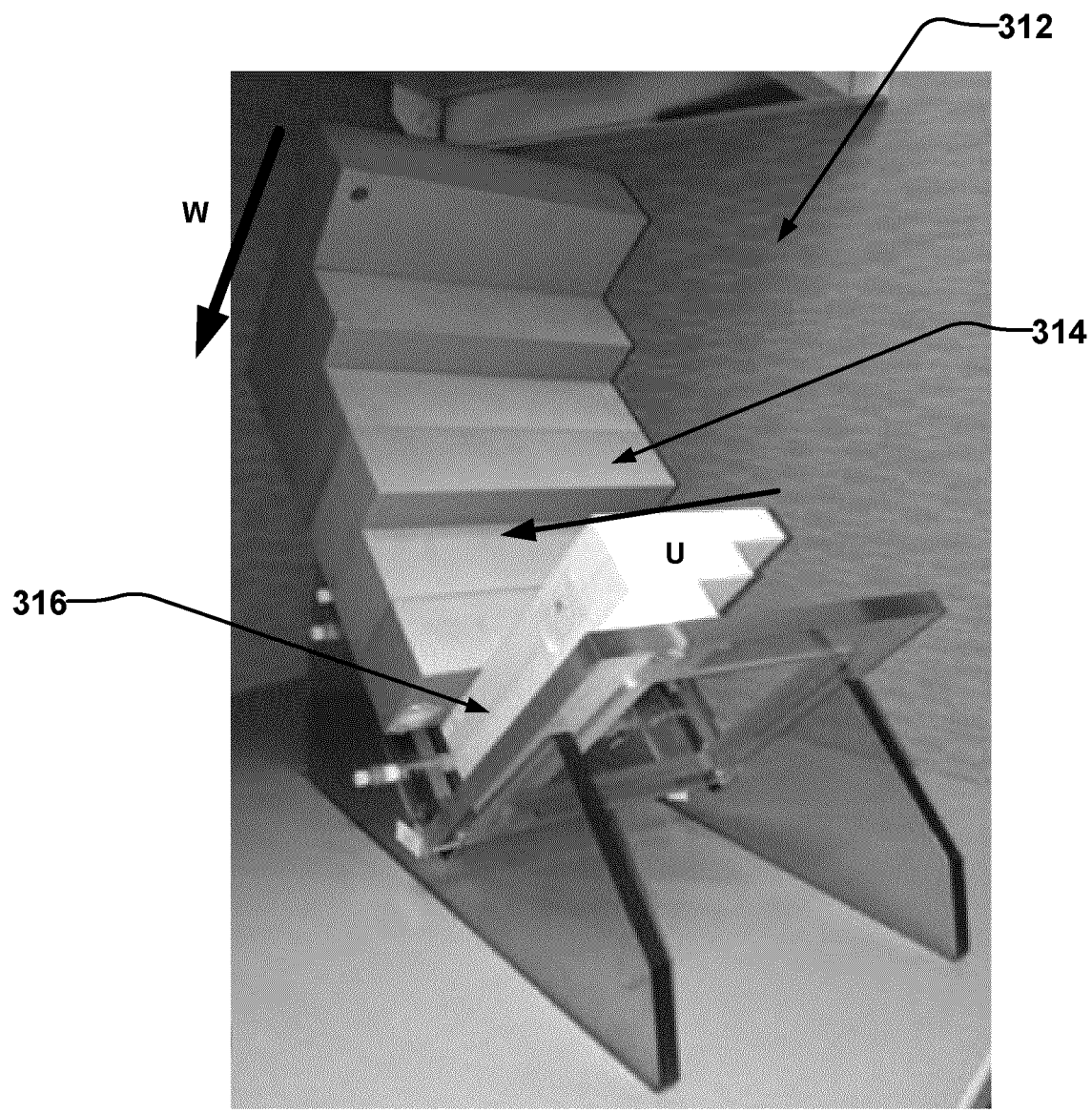
FIG. 5A is a perspective view of a step-phantom according to an example embodiment.

In block 310, step-phantom 312 is constructed. Step-phantom 312 may, for example, be as shown in FIG. 5A. Step-phantom 312 may comprise slabs of soft tissue mimicking materials 314 (e.g. Solid Water® slabs) and bone tissue mimicking material 316. Slabs 314, 316 may, for example, be stacked creating a step-like pattern. In some embodiments, thicknesses of soft tissue mimicking slabs 314 may range from 0 to 30 cm in direction W and thicknesses of bone tissue mimicking slabs 316 may range from 0 to 6 cm in direction U. The step phantom provides a number of different regions that can be imaged using lower energy and higher energy x-rays. Each region may provide a different combination of a thickness of soft-tissue mimicking material and a thickness of bone tissue mimicking material. The regions may, for example, be rectangular regions arranged in a rectangular grid pattern.

In some embodiments, soft tissue mimicking slabs 314 are commercially available GAMMEX™ model 557-450 slabs. In some embodiments, bone tissue mimicking slabs 316 are commercially available CIRS Inc., model BN30-20-AB slabs. In some embodiments, step phantom 312 is designed to match a field of view of an x-ray imaging device (e.g. device 510 described elsewhere herein).

A step phantom may optionally include tumor mimicking material. For example, a cylinder or sphere of tumor mimicking material may be included in each region. The tumor mimicking material may, for example, have a density intermediate that of the soft tissue mimicking material and the bone tissue mimicking material. As another example, the tumor mimicking material may have a density substantially similar (e.g. ±15%) to the density of water (e.g. to model lung tumors which may be very similar to soft tissue but not bone tissue). In some embodiments the tumor mimicking material may comprise Solid Water® slabs. The tumor mimicking material may optionally have x-ray properties that are selected to match those of a specific type of tumor of interest. Including tumor mimicking material in the step phantom may allow identification of weighting factors suitable for enhancing contrast of tumors in dual energy x-ray images. These weighting factors may differ from weighting factors intended for other purposes such as deemphasizing bone tissue or deemphasizing soft tissue.

In block 320, higher energy image 322 and lower energy image 324 of step-phantom 312 are acquired. Optionally, dark images 326 and/or flood images 328 may be acquired. Higher and lower energy images 322, 324, optional dark images 326 and optional flood images 328 are collectively referred to herein as step-phantom images 321.

Step-phantom images 321 may be acquired in any order. For example, step-phantom images 321 may be acquired by first acquiring one or more higher energy images 322, followed by acquiring one or more lower energy images 324, followed by acquiring one or more dark images 326 and concluding by acquiring one or more flood images 328. In a second non-limiting illustrative example, step-phantom images 321 may be acquired by first acquiring one or more dark images 326, followed by acquiring one or more flood images 328, followed by acquiring one or more lower energy images 324 and concluding by acquiring one or more higher energy images 322.

Step-phantom 312 may be positioned to face a radiation source (e.g. radiation source 520 described elsewhere herein). In some embodiments, step-phantom 312 is placed on a treatment couch which is rotated at a given angle for step-phantom 312 to face the radiation source. Alternatively, or in addition, step-phantom 312 may be positioned for a central axis of a radiation beam emitted from the radiation source to be perpendicular to a surface of step-phantom 312. This may be achieved, for example, by placing step-phantom 312 on an angled plastic stand. In one embodiment, the plastic stand is angled 42° relative to a surface plane of the treatment couch (e.g. for a Brainlab™ ExacTrac™ System).

Higher and lower energy images 322, 324 may be acquired in a manner, and/or comprise properties, identical to higher and lower energy images 122, 124 described elsewhere herein. Dark images 326 may be acquired by blocking an x-ray radiation source (e.g. radiation source 520 described elsewhere herein) with a material such as lead. Flood images 328 may be acquired by directly (i.e. with no interference) exposing a radiation detector (e.g. detector 530 described elsewhere herein) to a radiation beam (e.g. by moving a treatment couch away from a radiation beam path). In some embodiments, higher and lower energy flood images 328A and 328B respectively are acquired. Higher energy flood image 328A may, for example, be acquired using a peak x-ray tube voltage of 120 kVp and an x-ray tube current of 0.63 mAs. Lower energy flood image 328B may, for example, be acquired using a peak x-ray tube voltage of 60 kVp and an x-ray tube current of 12.68 mAs.

To avoid saturation of a detector (e.g. detector 530 described elsewhere herein), a plurality of lower x-ray radiation dose higher and/or lower energy images 322, 324 may be acquired. For the purposes of the technology described herein, radiation dose generally corresponds to an amount of radiation an object is exposed to over a period of time. Radiation dose may, for example, be given in units of mAs (e.g. corresponding to an x-ray tube current), rads, rems, roentgens, sieverts, grays or the like. In some embodiments, 12 lower x-ray radiation dose higher energy images 322 (each acquired using an x-ray tube current of 0.99 mAs) are acquired and added together. In some embodiments, four lower x-ray radiation dose lower energy images 324 (each acquired using an x-ray radiation dose of 9.9 mAs) are acquired and added together.

In block 330, higher and lower energy images 322, 324 are optionally conditioned. Effects of dark signals (e.g. noise from underexposure of a detector) on images 322, 324 may, for example, be removed by subtracting one or more dark images 326 from images 322, 324. Effects of flood signals (e.g. noise from overexposure of a detector) on higher energy images 322 may, for example, be removed by dividing higher energy images 322 by one or more higher energy flood images 328A. Effects of flood signals on lower energy images 324 may, for example, be removed by dividing lower energy images 324 by one or more lower energy flood images 328B.

Figure 5B:
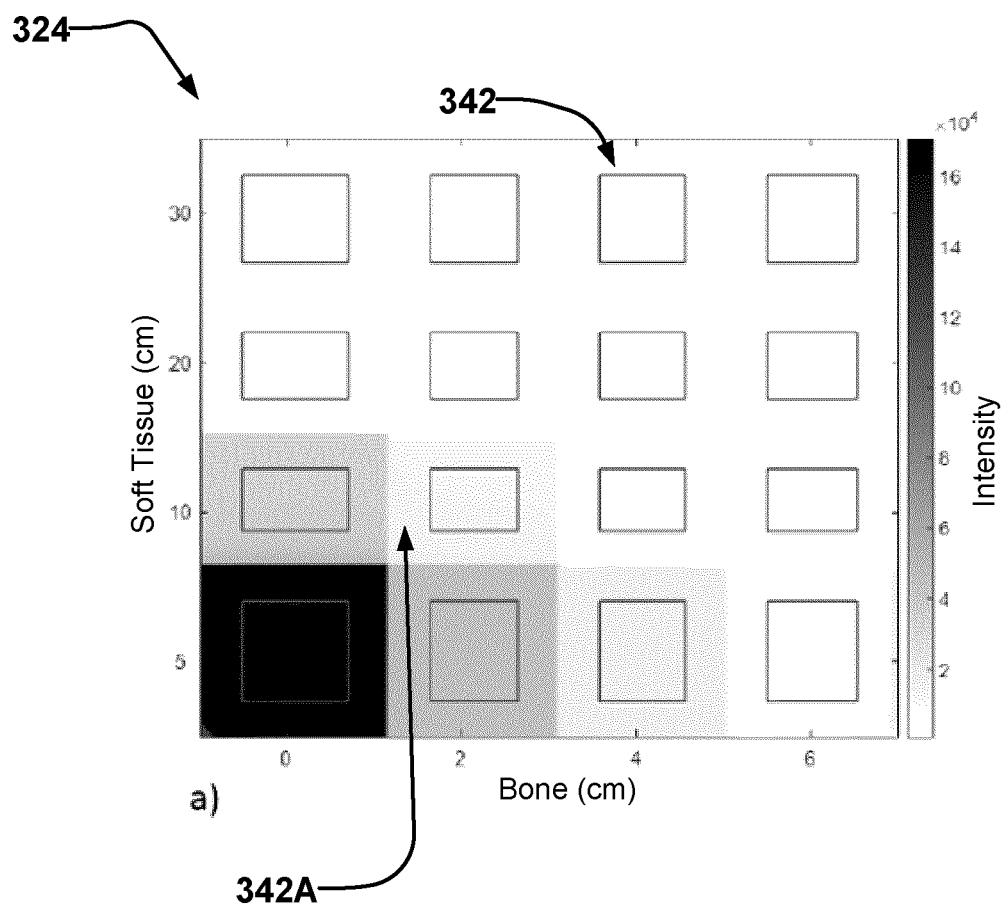
FIG. 5B illustrates different regions of interest according to an example embodiment.

In block 340, higher and/or lower energy images 322, 324 are separated into discrete regions of interest (ROIs) 342. Each ROI 342 represents a region of images 322, 324 corresponding to a discrete thickness of soft tissue mimicking material 314 and a discrete thickness of bone tissue mimicking material 316. FIG. 5B shows an example lower energy image 324 of step-phantom 312 separated into 16 discrete ROIs 342. For example, ROI 342A corresponds to a region of image 324 associated with a 10 cm thickness of soft tissue mimicking materials 314 and a 2 cm thickness of bone tissue mimicking material 316.

In some embodiments, each ROI 342 is identified based on changes in pixel values (e.g. a first ROI 342 may have distinct pixel values different from second ROI 342). In some embodiments, each ROI 342 is identified by selecting a region of one or more pixels of higher and lower energy images 322, 324.

In block 350, a weighting value $\omega_{optimized}$ that is optimized for a particular purpose (e.g. to de-emphasize a tissue type such as soft tissue 52, bone tissue 54, or the like) within an ROI 342 corresponding to a particular combination of thicknesses of different tissue types is determined. Optimizing weighting value $\omega_{optimized}$ may, for example, correspond to generating a contrast-to-noise ratio (CNR) that is as close to zero as possible.

As another example, $\omega_{optimized}$ may be selected to enhance contrast of tumor tissue. In this case optimizing weighting value $\omega_{optimized}$ may, for example, correspond to generating a contrast-to-noise ratio (CNR) for the area corresponding to tumor tissue that is maximized.

In some embodiments block 350 determines two or more values for $\omega_{optimized}$ for each region of interest. For example, block 350 may determine values of two or more of: $\omega_{bMin}$ selected to deemphasize bone tissue, $\omega_{tmin}$ selected to deemphasize soft tissue, and $\omega_{Tmax}$ selected to maximize tumor contrast. In some embodiments block 350 determines different sets of values for $\omega_{Tmax}$ for different types of tumor tissue.

In some embodiments, higher and lower energy images 322, 324 are combined to generate dual energy image 355 of step-phantom 312 using Equation (9) or a mathematical equivalent thereof:

$$\ln(I_{DE}) = \ln(I_{HE}) - \omega_{intermediate} \ln(I_{LE}) \quad (9)$$

where $I_{DE}$ represents pixel intensities of generated dual energy image 355, $I_{HE}$ represents pixel intensities of higher energy image 322, $\omega_{intermediate}$ represents a weighting factor value being determined and $I_{LE}$ represents pixel intensities of lower energy image 324. In some embodiments, an anti-correlated noise reduction algorithm may be applied during the generation of dual energy image 355.

In some embodiments, values of $\omega_{intermediate}$ are iteratively incremented. In such embodiments, values of $\omega_{intermediate}$ may, for example, iteratively be incremented in 0.01 increments from 0 to 1.60. In some embodiments, values of $\omega_{intermediate}$ are iteratively decremented. In some embodiments, values of $\omega_{intermediate}$ are chosen using an alternative search strategy such as using variable increments and/or variable decrements and/or random choices.

In some embodiments, optimized weighting value $\omega_{optimized}$ is the value of $\omega_{intermediate}$ which results in a CNR between: a ROI 355A of generated dual energy image 355 de-emphasizing a tissue type 356 (not expressly shown) and a ROI 355B of generated dual energy image 355 not comprising de-emphasized tissue type 356, being as close to zero as possible. ROI 355B is identical to ROI 355A (i.e. thicknesses of imaged tissue types are identical) except that ROI 355B does not include tissue type 356 to be de-emphasized. A CNR value close to zero may, for example, indicate that there is a very small difference between ROIs 355A and 355B suggesting successful deemphasis of tissue type 356. A CNR between a region 355A including soft tissue 52 having thickness J and de-emphasized bone tissue 54 having thickness K and a region 355B including soft tissue 52 having thickness J only may, for example, be represented as:

$$CNR_{bst,st} = \frac{I_{bst} - I_{st}}{\sqrt{\left(\frac{1}{2}\right)(\sigma_{bst}^2 + \sigma_{st}^2)}} \quad (10)$$

where $I_{bst}$ and $I_{st}$ are the average intensities of ROI 355A and ROI 355B respectively, and $\sigma_{bst}$ and $\sigma_{st}$ are corresponding standard deviations.

By way of additional non-limiting examples, the CNR between region 355A including soft tissue 52 having thickness J and de-emphasized bone tissue 54 having thickness K and region 355B including soft tissue 52 having thickness J only may be represented as:

$$CNR_{bst,st} = \frac{I_{bst} - I_{st}}{\sigma_{st}}; \text{ or} \quad (11)$$

$$CNR_{bst,st} = \frac{|I_{bst} - I_{st}|}{\sigma_{st}}. \quad (12)$$

Figure 5C:
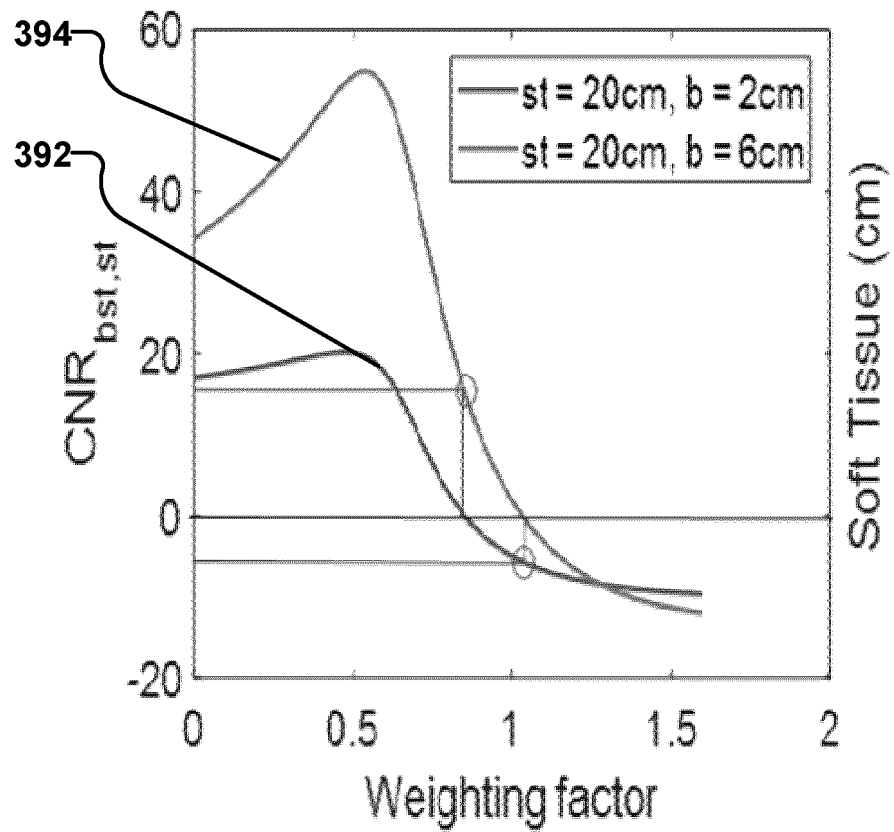
FIG. 5C illustrates example contrast-to-noise ratio values as a function of weighting value.
Figure 5D:
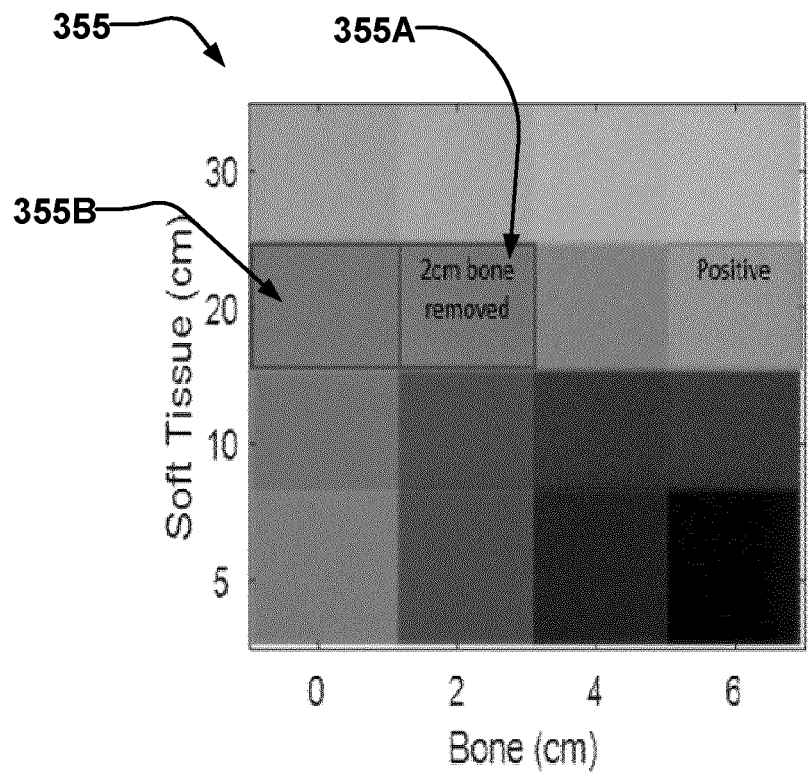
FIGS. 5D and 5E illustrate example dual energy generated images.
Figure 5E:
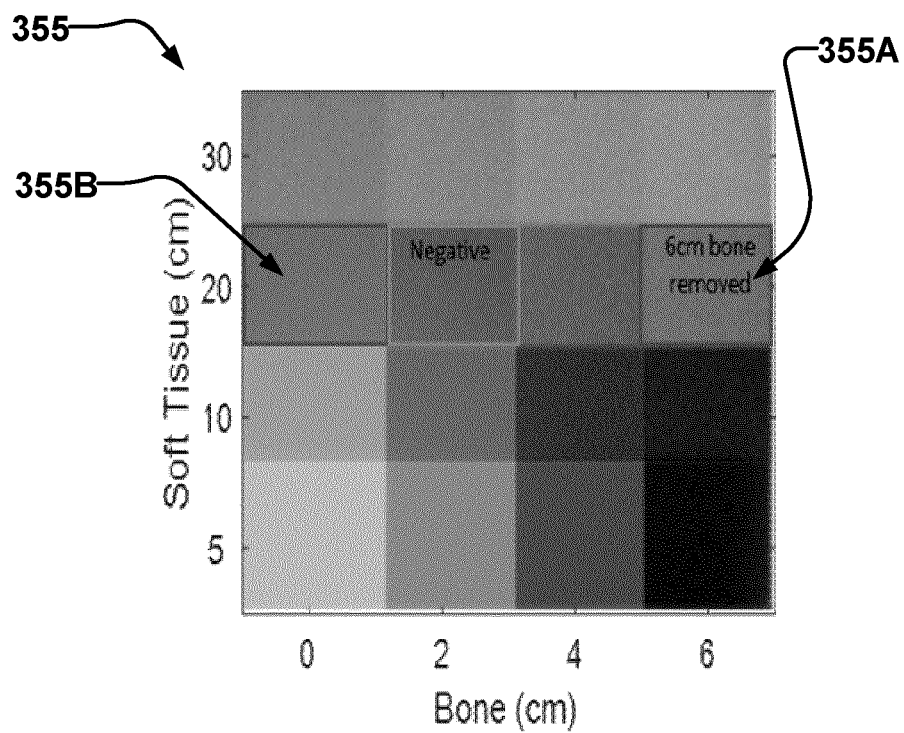

FIG. 5C is a graph of example CNR as a function of weighting factor (e.g. such as weighting factor $\omega_{intermediate}$) for one example imaging system. Curve 392 corresponds to an ROI having 2 cm of bone mimicking material 316 and 20 cm of soft tissue mimicking material 314. For such tissue thicknesses in the example case of FIG. 5C, $\omega_{optimized}$ for de-emphasizing of 2 cm of bone tissue 54 is a value of 0.86 (i.e. when CNR=0). FIG. 5D illustrates a dual energy image 355 generated to de-emphasize bone tissue 54 using a weighting value of 0.86 applied to each pixel of higher or lower energy images 322, 324. As shown in FIG. 5D, only ROI 355A matches ROI 355B. Curve 394 corresponds to an ROI having 6 cm of bone mimicking material 316 and 20 cm of soft tissue mimicking material 314. For such tissue thicknesses in the example case of FIG. 5C, $\omega_{optimized}$ for de-emphasizing 6 cm of bone tissue 54 is a value of 1.03 (i.e. when CNR=0). FIG. 5E illustrates a dual energy image 355 generated to de-emphasize bone tissue 54 using a weighting value of 1.03 applied to each pixel of higher or lower energy images 322, 324. As shown in FIG. 5E, only ROI 355A matches ROI 355B.

Block 360 optionally returns method 300 to block 350 to calculate an optimized weighting value $\omega_{optimized}$ for a different ROI 342 (i.e. another ROI 342 comprising tissue thicknesses different from those of the already selected ROI(s) 342 for which an optimized weighting value $\omega_{optimized}$ has been determined).

In block 370, one or more optimized weighting values $\omega_{optimized}$ are recorded. In some embodiments, optimized weighting values $\omega_{optimized}$ may be recorded in memory (e.g. memory 544 of computer 540 described elsewhere herein).

In some embodiments, scatter effects on higher energy images 322, 324 are ascertained by modifying step-phantom 312, for example, to include a tray of pins. The pins may be made of steel, lead, a material other than lead having a high atomic number or the like. The tray may be positioned such that a pin is centered in each ROI 342 of higher and lower energy images 322, 324.

In some embodiments, weighting factor values 142 may be determined computationally. Weighting factor values 142 may be computed differently based on how one or more tissue types are to be de-emphasized in dual energy image 105. In some embodiments, a tissue type to be de-emphasized is effectively replaced with a thickness of a tissue type not being de-emphasized. In some embodiments, a tissue type to be de-emphasized is effectively replaced with air (i.e. can be modeled as a tissue having a thickness of 0).

In embodiments where a tissue type to be de-emphasized is effectively replaced with air, an ideal weighting factor value 142 for de-emphasizing bone tissue 54 may, for example, be represented as:

$$\omega = \frac{\mu_H^b}{\mu_L^b} \quad (13)$$

where $\omega$ is an ideal weighting for de-emphasizing bone and $\mu_H^b$ and $\mu_L^b$ are the linear attenuation coefficients for bone tissue for high and low energies respectively.

In embodiments where radiation beams 112, 114 are polyenergetic x-ray radiation beams, beam hardening effects as radiation beams 112, 114 pass through tissue region 110 may be accounted for by modifying Equation (13) described above to account for hardened x-ray radiation spectra as follows:

$$\omega = \frac{\bar{\mu}_H^b}{\bar{\mu}_L^b} \quad (14)$$

where $\bar{\mu}$ is a detector (e.g. detector 530 described elsewhere herein) spectrum weighted linear attenuation coefficient for either a high energy radiation beam 112 or low energy x-ray radiation beam 114 and may, for example, be expressed as:

$$\bar{\mu} = \frac{\int \phi(E)\mu(E)dE}{\int \phi(E)dE} \quad (15)$$

where $\phi(E)$ is the fluence spectrum after passing through soft tissue 52 and bone tissue 54, and $\mu(E)$ is the linear attenuation coefficient for average adult bone.

To account for scatter effects, Equation (14) described herein may be modified as follows:

$$\omega = \frac{\bar{\mu}_H^b b + \ln\left(\frac{1 + S_H(t, 0)}{1 + S_H(t, b)}\right)}{\bar{\mu}_L^b b + \ln\left(\frac{1 + S_L(t, 0)}{1 + S_L(t, b)}\right)} \quad (16)$$

where $S_H(t, b)$ and $S_L(t, b)$ are the scatter to primary ratios for both higher and lower energy x-ray radiation beams 112, 114 for a given patient P geometry at a fixed location in an image with (t, b) thickness of soft tissue 52 and bone tissue 54. In some embodiments, the scatter to primary ratios for a given patient geometry may be obtained using Monte Carlo simulation.

In some embodiments, the Monte Carlo simulation comprises simulating tissues and their corresponding geometries on a beam path. Such simulation may, for example, include simulating properties corresponding to an x-ray tube and/or radiation source used to generate higher and/or lower energy radiation beams 112, 114, interactions of higher and/or lower energy radiation beams 112, 114 within patient P and/or properties corresponding to an x-ray detector used to detect higher and/or lower energy radiation beams 112, 114. The Monte Carlo simulation may model both the higher and/or lower energy radiation beams as well as secondary radiation beams (e.g. scatter radiation beams corresponding to higher and/or lower energy radiation beams 112, 114).

Due to beam hardening of a radiation beam as it passes through a patient P, detector response may vary (e.g. a response of, for example, detector 530 described elsewhere herein). To account for effects of a detector response, Equation (14) described herein may be modified as follows:

$$\omega = \frac{\bar{\mu}_H^b b + \ln\left(\frac{\alpha_H(t, 0)E_H(t, 0)}{\alpha_H(t, b)E_H(t, b)}\right)}{\bar{\mu}_L^b b + \ln\left(\frac{\alpha_L(t, 0)E_L(t, 0)}{\alpha_L(t, b)E_L(t, b)}\right)} \quad (17)$$

where $\alpha_H$ and $E_H$ respectively are detective quantum efficiency and absorbed energy per interaction, at a fixed location in the image with (t,b) thicknesses of soft tissue 52 and bone tissue 54 for higher energy radiation beam 112 and $\alpha_L$ and $E_L$ respectively are detective quantum efficiency and absorbed energy per interaction, at a fixed location in the image with (t,b) thicknesses of soft tissue 52 and bone tissue 54 for lower energy radiation beam 114.

Combining effects of beam hardening (e.g. Equations (14) and (15)), scattering (e.g. Equation (16)) and detector response (e.g. Equation (17)), bone tissue 54 de-emphasizing weighting factor values 142 may be represented as:

$$\omega = \frac{\bar{\mu}_H^b b + \ln\left(\frac{\alpha_H(t, 0)E_H(t, 0)(1 + S_H(t, 0))}{\alpha_H(t, b)E_H(t, b)(1 + S_H(t, b))}\right)}{\bar{\mu}_L^b b + \ln\left(\frac{\alpha_L(t, 0)E_L(t, 0)(1 + S_L(t, 0))}{\alpha_L(t, b)E_L(t, b)(1 + S_L(t, b))}\right)} \quad (18)$$

Soft tissue 52 de-emphasizing weighting factor values 142 for de-emphasizing soft tissue 52 by effectively replacing soft tissue 52 with air may similarly, for example, be represented as:

$$\omega_b = \frac{\bar{\mu}_H^b t + \ln\left(\frac{\alpha_H(0, b)E_H(0, b)(1 + S_H(0, b))}{\alpha_H(t, b)E_H(t, b)(1 + S_H(t, b))}\right)}{\bar{\mu}_L^b b + \ln\left(\frac{\alpha_L(0, b)E_L(0, b)(1 + S_L(0, b))}{\alpha_L(t, b)E_L(t, b)(1 + S_L(t, b))}\right)} \quad (19)$$

where $\bar{\mu}_H^t$ and $\bar{\mu}_L^t$ are the linear attenuation coefficients for soft tissue 52 for higher and lower energies respectively with detector response as described herein considered.

In embodiments where, for example, bone tissue 54 to be de-emphasized is effectively replaced with a tissue type not being de-emphasized having thickness $b_0$ (e.g. soft tissue 52), Equations (13), (14) and (16) to (18) may be replaced with Equations (20) to (24) respectively. Equations (20) to (24) may, for example, be represented as follows:

$$\omega = \frac{(\mu_H^b b - \mu_H^t b_0)}{(\mu_L^b b - \mu_L^t b_0)} \quad (20)$$

$$\omega = \frac{(\bar{\mu}_H^b b - \bar{\mu}_H^t b_0)}{(\bar{\mu}_L^b b - \bar{\mu}_L^t b_0)} \quad (21)$$

$$\omega = \frac{\bar{\mu}_H^b b - \bar{\mu}_H^t b_0 + \ln\left(\frac{1 + S_H(t + b_0, 0)}{1 + S_H(t, b)}\right)}{\bar{\mu}_L^b b - \bar{\mu}_L^t b_0 + \ln\left(\frac{1 + S_L(t + b_0, 0)}{1 + S_L(t, b)}\right)} \quad (22)$$

$$\omega = \frac{\bar{\mu}_H^b b - \bar{\mu}_H^t b_0 + \ln\left(\frac{\alpha_H(t + b_0, 0)E_H(t + b_0, 0)}{\alpha_H(t, b)E_H(t, b)}\right)}{\bar{\mu}_L^b b + \ln\left(\frac{\alpha_L(t + b_0, 0)E_L(t + b_0, 0)}{\alpha_L(t, b)E_L(t, b)}\right)} \quad (23)$$

$$\omega = \frac{\bar{\mu}_H^b b - \bar{\mu}_H^t b_0 + \ln\left(\frac{\alpha_H(t + b_0, 0)E_H(t + b_0, 0)(1 + S_H(t + b_0, 0))}{\alpha_H(t, b)E_H(t, b)(1 + S_H(t, b))}\right)}{\bar{\mu}_L^b b - \bar{\mu}_L^t b_0 + \ln\left(\frac{\alpha_L(t + b_0, 0)E_L(t + b_0, 0)(t + b_0, 0))}{\alpha_L(t, b)E_L(t, b)(1 + S_L(t, b))}\right)} \quad (24)$$

In some embodiments, thickness $b_0$ is equal to bone thickness b.

In some embodiments, soft tissue 52 to be de-emphasized is effectively replaced with a tissue type not being de-emphasized having thickness $t_0$ (e.g. bone tissue 54). In such embodiments, Equation (19) may be replaced with Equation (25) which may be represented as follows:

$$\omega = \frac{\bar{\mu}_H^b t - \bar{\mu}_H^t t_0 + \ln\left(\frac{\alpha_H(0, b + t_0)E_H(0, b + t_0)(1 + S_H(0, b + t_0))}{\alpha_H(t, b)E_H(t, b)(1 + S_H(t, b))}\right)}{\bar{\mu}_L^b t - \bar{\mu}_L^t t_0 + \ln\left(\frac{\alpha_L(0, b + t_0)E_L(0, b + t_0)(1 + S_L(0, b + t_0))}{\alpha_L(t, b)E_L(t, b)(1 + S_L(t, b))}\right)} \quad (25)$$

In some embodiments, thickness $t_0$ is equal to soft tissue thickness t.

In some embodiments, scatter of radiation beams 112, 114 may, for example, be removed or reduced by using an anti-scatter grid.

Figure 6:
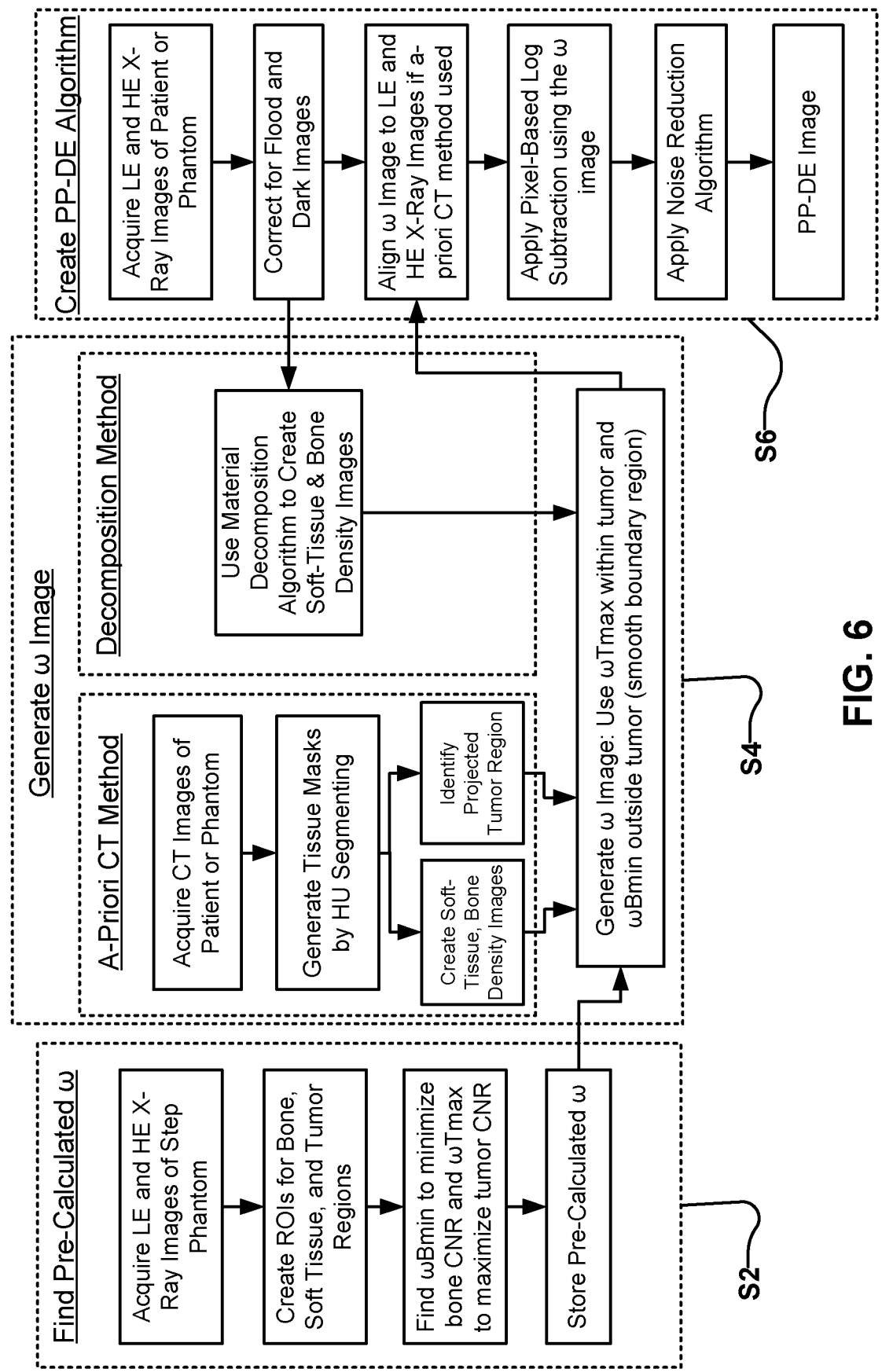
FIG. 6 is a data flow diagram illustrating a method according to an example embodiment.
Figure 6A:
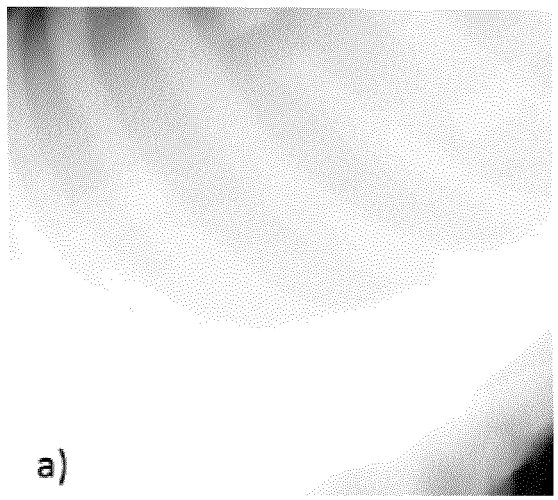
FIGS. 6A to 6D illustrate example x-ray images.
Figure 6B:
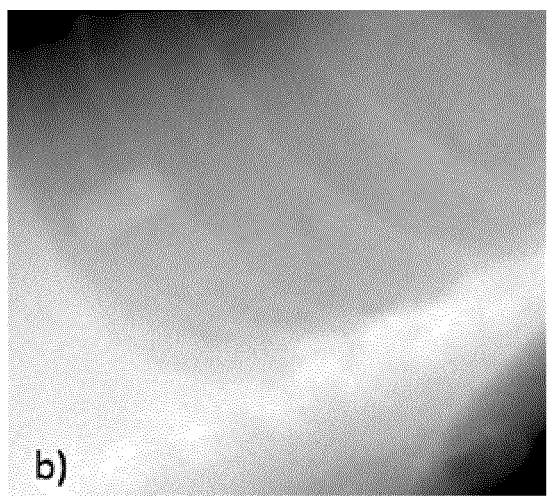
Figure 6C:
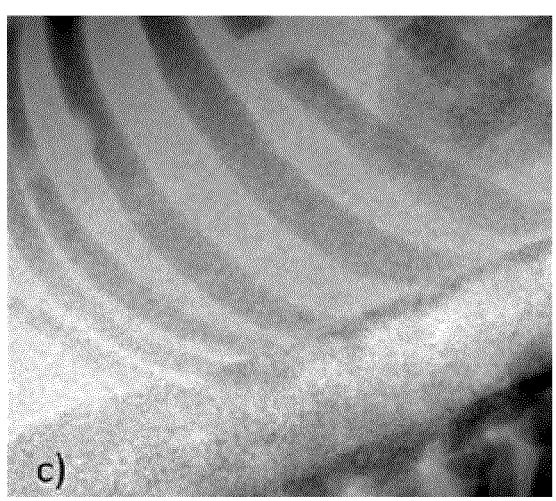
Figure 6D:
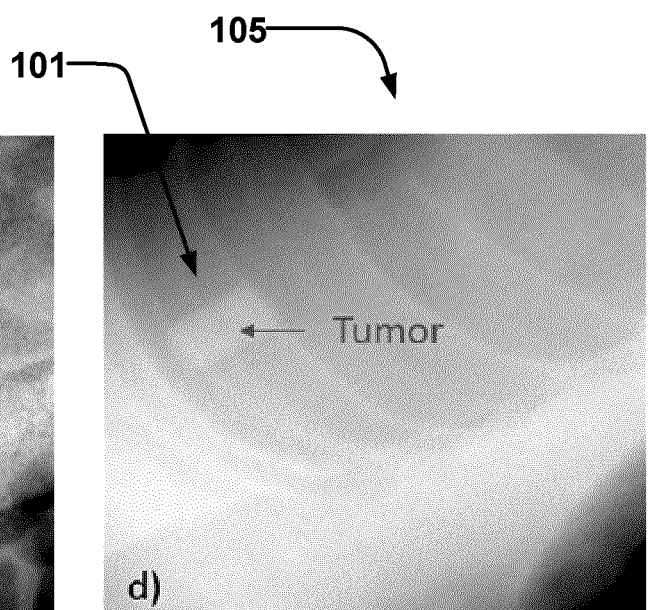

FIG. 6A illustrates a conventional clinical single energy x-ray image of patient P's thorax. FIG. 6B illustrates a conventional dual energy x-ray image of patient P's thorax de-emphasizing ribs but not vertebrae. FIG. 6C illustrates a conventional dual energy x-ray image of patient P's thorax de-emphasizing vertebrae but not ribs. FIG. 6D illustrates a dual energy x-ray image 105 of patient P's thorax with both ribs and vertebrae de-emphasized (e.g. de-emphasizing of bone tissue 54) generated according to the methods described herein. As illustrated by FIG. 6D, visibility of a target tissue such as a tumor 101 may be enhanced in dual energy image 105.

As mentioned above, weighting factors can be selected to achieve any of a range of desired objectives such as de-emphasizing bony tissue, de-emphasizing soft tissue or enhancing the contrast of a specific tissue type relative to one or more other tissue types.

In some cases it may be desired to select weighting factors to achieve different goals in different parts of one combined image. For example, de-emphasizing one tissue type may be most important in some parts of the combined image and enhancing contrast of a tissue type may be most important in other parts of the combined image.

Figure 5G:
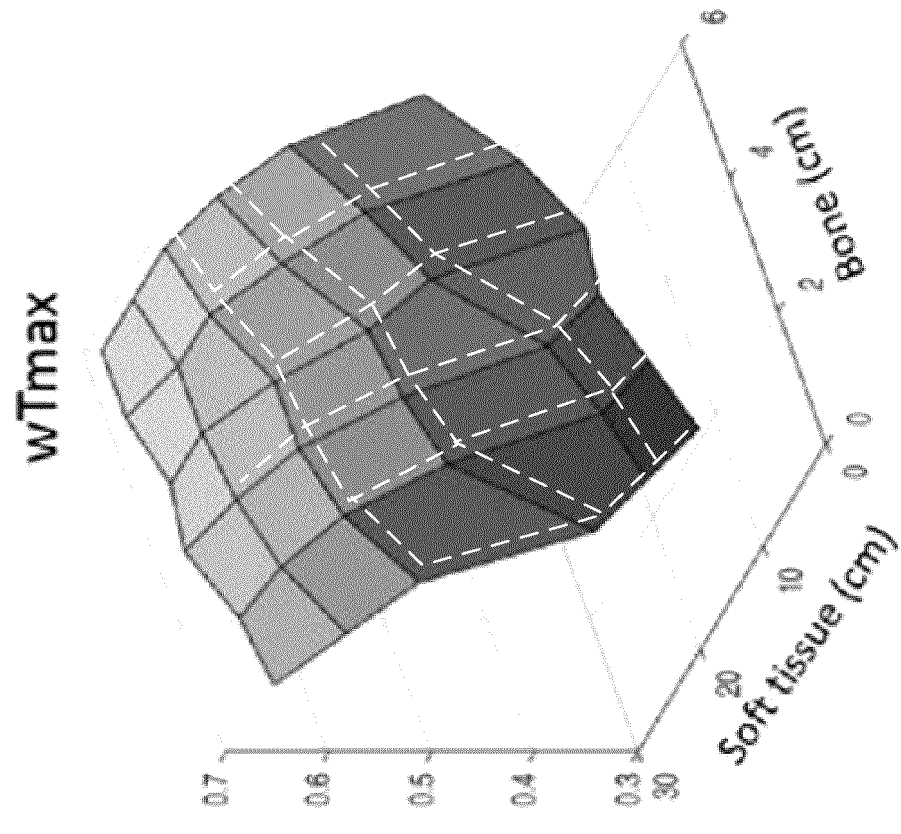
FIGS. 5F and 5G respectively show example weighting factors for optimally deemphasizing bone and example weighting factors for optimally emphasizing contrast of tumors.
Figure 5F:
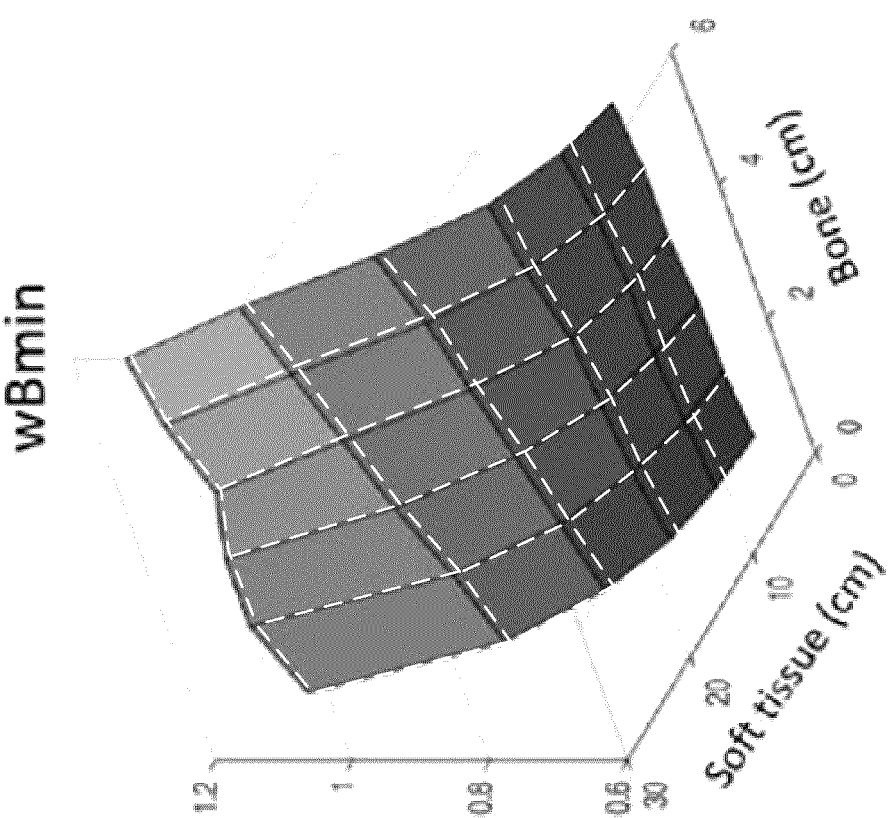

For example, de-emphasizing bone tissue (e.g. bone tissue 54) may be most important in some parts of the combined image and enhancing contrast of one or more tumors in tissue region 110 may be most important in a part of the combined image which includes the tumors. For any pixel the weighting factors for achieving these goals may have different values. This is illustrated in FIGS. 5F and 5G. FIG. 5F shows weighting values optimized for deemphasizing bone tissue for various combinations of thicknesses of bone tissue and soft tissue. FIG. 5G shows weighting values optimized for enhancing tumor contrast for the same combinations of thickness of bone tissue and soft tissue. It can be observed by casual inspection that the weighting values in FIGS. 5F and 5G are not the same.

Figures 5H, 5I:
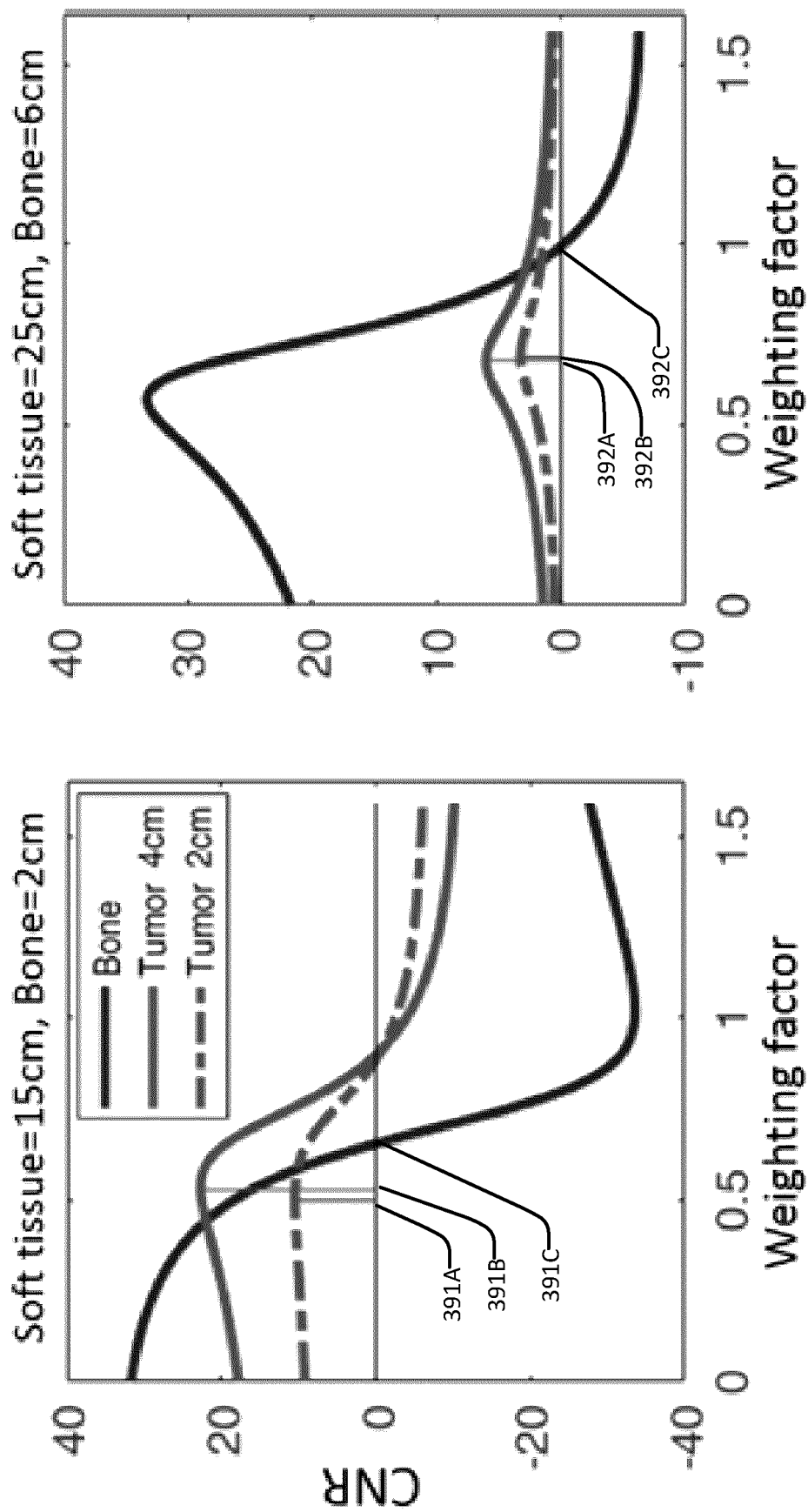
FIGS. 5H and 5I are graphs of CNR for bone tissue and two thicknesses of tumor tissue as a function of weighting factor.

FIGS. 5H and 5I are plots of CNR vs weighting factor for bone tissue, tumor tissue having a thickness of 4 cm and tumor tissue having a thickness of 2 cm for two sample regions having different overall thicknesses of bone tissue and soft tissue. Optimal deemphasizing of bone tissue is achieved when the CNR for bone is zero. Optimal weighting for maximizing tumor contrast is achieved when the curve for the tumor CNR is maximized. FIG. 5H is for the case of 15 cm of soft tissue and 2 cm of bone. Optimized weighting values 391A and 391B respectively maximize contrast for thicker (4 cm) and thinner (2 cm) tumor tissue. Optimized weighting value 391C deemphasizes bone tissue.

FIG. 5I is for the case of 25 cm of soft tissue and 6 cm of bone tissue. Optimized weighting values 392A and 392B respectively maximize contrast for thicker (4 cm) and thinner (2 cm) tumor tissue. Optimized weighting value 392C deemphasizes bone tissue.

In some embodiments two or more different sets of weighting factors are determined. The different sets of weighting factors may each be determined to achieve a different goal. For example, a first set of weighting factors may be selected to optimally de-emphasize bone tissue while a second set of weighting factors may be selected to optimally maximize tumor contrast. Weighting factors from the first set may be used to determine pixel values for some parts of the combined image and weighting factors from the second set may be used to determine pixel values for other parts of the combined image. The weighting factor for any pixel (whether it is from the first set or the second set) may be applied to determine the corresponding pixel value for the combined image as described elsewhere herein.

In some embodiments the image portions to which different sets of weighting factors are to be applied are selected based on data regarding the distribution of certain types of tissue. For example, information about the distribution of one or more tissues within region 110 may be ascertained from imaging data such as MRI data, CT data and/or the like as described elsewhere herein. For example, the distribution of tumor tissue within region 110 may be determined from a CT scan or MRI. Weighting values from one set may be used for regions containing tumor tissue and weighting values from another set may be used for other parts of the combined image.

In some embodiments the image portions to which different sets of weighting factors are to be applied are selected based on human input and/or image analysis. For example, an initial combined image may be prepared using an initial set of weighting factors. A person (e.g. a radiologist) may inspect the initial combined image to identify portions of the combined image that appear to contain tumor tissue (or another tissue type of interest). The person may indicate such portions using a suitable interface device such as a stylus. As another option the person may identify the portions by viewing a single energy x-ray image. A new combined image may then be created in which different sets of weighting factors are used within and outside of the identified portions. Optionally one of the different sets of weighting factors is the initial set of weighting factors.

As another example, human input may be replaced or augmented by image analysis of the initial combined image. For example a neural network trained on tumor images may process the initial combined image to identify portions which appear as if they are likely to contain tumor tissue.

In a way described above or in other ways, the area of an x-ray image of tissue region 110 may be divided into a first portion in which x-rays do not pass through tumor tissue and a second portion in which the x-rays pass through a part of tissue region 110 that includes tumor tissue. In one such example case, one set of weighting factors is applied to combining lower and higher energy x-rays in the first portion to optimally de-emphasize bone tissue while a second set of weighting factors is applied to the second portion to maximize contrast of the tumor tissue.

In some embodiments a smoothing technique is applied to smoothly transition between portions in which different sets of weighting factors are used to create a combined image. "Smoothly" means that two adjacent sets of weighting factors gradually transition from one to another as one moves across an image. Any known smoothing technique may be used. In some embodiments the smoothing technique is adjusted in real time. The smoothing technique may be linear or non-linear. The smoothing technique may be adjusted autonomously or manually by an operator. The smoothing technique may be adjusted linearly or non-linearly.

For example a margin may be defined at boundaries between different portions of a combined image. Weighting factors from a first set of weighting factors designed to achieve a first goal may be used in first regions. Weighting factors from a second set of weighting factors designed to achieve a second goal may be used in second regions. In the margins along boundaries of the first and second regions the weighting factors may be interpolated.

The interpolation may be based on a distance from the boundary. For example, a margin may be a suitable number of pixels (e.g. 100 pixels) wide. At a first edge of the margin the first set of weighting factors may be used. At the opposing second edge of the margin the second set of weighting factors may be used. At pixels in the margin between the first and second edges a linear or non-linear interpolation which combines values from the first and second sets is used.

In a simple example the value used may be obtained by:

$$\frac{x}{M}(\omega_1) + \left(\frac{M-x}{M}\right)(\omega_2) = \omega_{interpolated} \tag{26}$$

where M is the width of the margin (e.g. in pixels), x is a distance that a current pixel is across the width of the margin starting from the first edge, $\omega_1$ is the weighting factor for the current pixel from the first set of weighting factors, $\omega_2$ is the weighting factor for the current pixel from the second set of weighting factors, and $\omega_{Interpolated}$ is the interpolated weighting factor for the current pixel which will be used to generate the combined image.

Figure 5J:
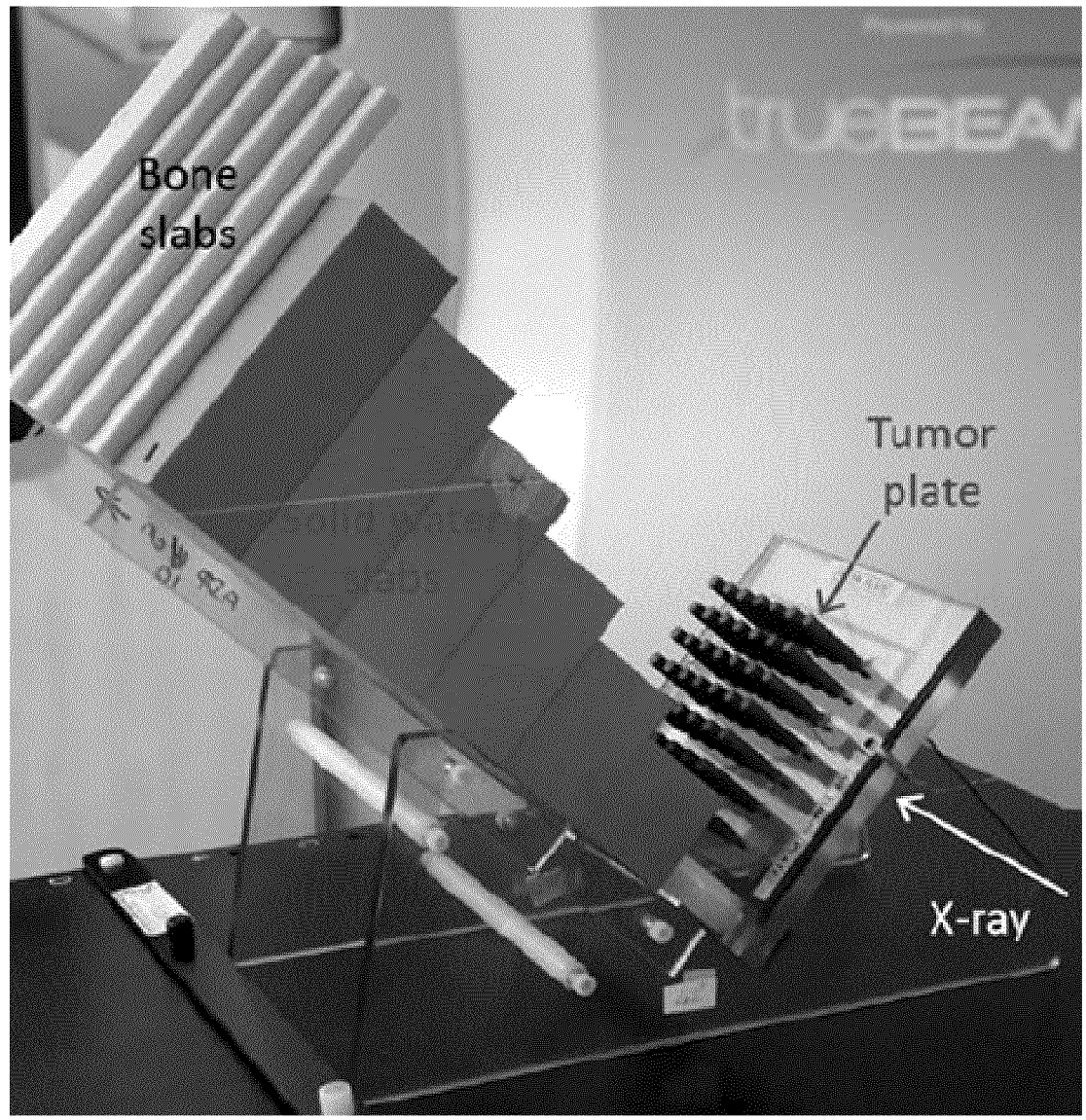
FIG. 5J is a perspective view of a step-phantom according to an example embodiment.

Pre-calibrated sets of weighting factors may be determined by processing data collected by imaging one or more tissue models using radiation beams 112 and 114 as described elsewhere herein. In some embodiments the tissue models comprise materials that simulate soft tissue, bone tissue and tumor tissue (e.g. as shown in FIG. 5J). The pre-calibrated sets of weighting factors may have values that vary based on tissue thicknesses. For example, the pre-calibrated sets may comprise larger values as tissue thicknesses increase (e.g. as a result of beam hardening of radiation beams 112 and/or 114). In some embodiments a pre-calibrated set of weighting factors is optimized to either eliminate a tissue type (e.g. bone or soft tissue) or to maximize contrast of a tissue type (e.g. tumor tissue).

Figure 5K:
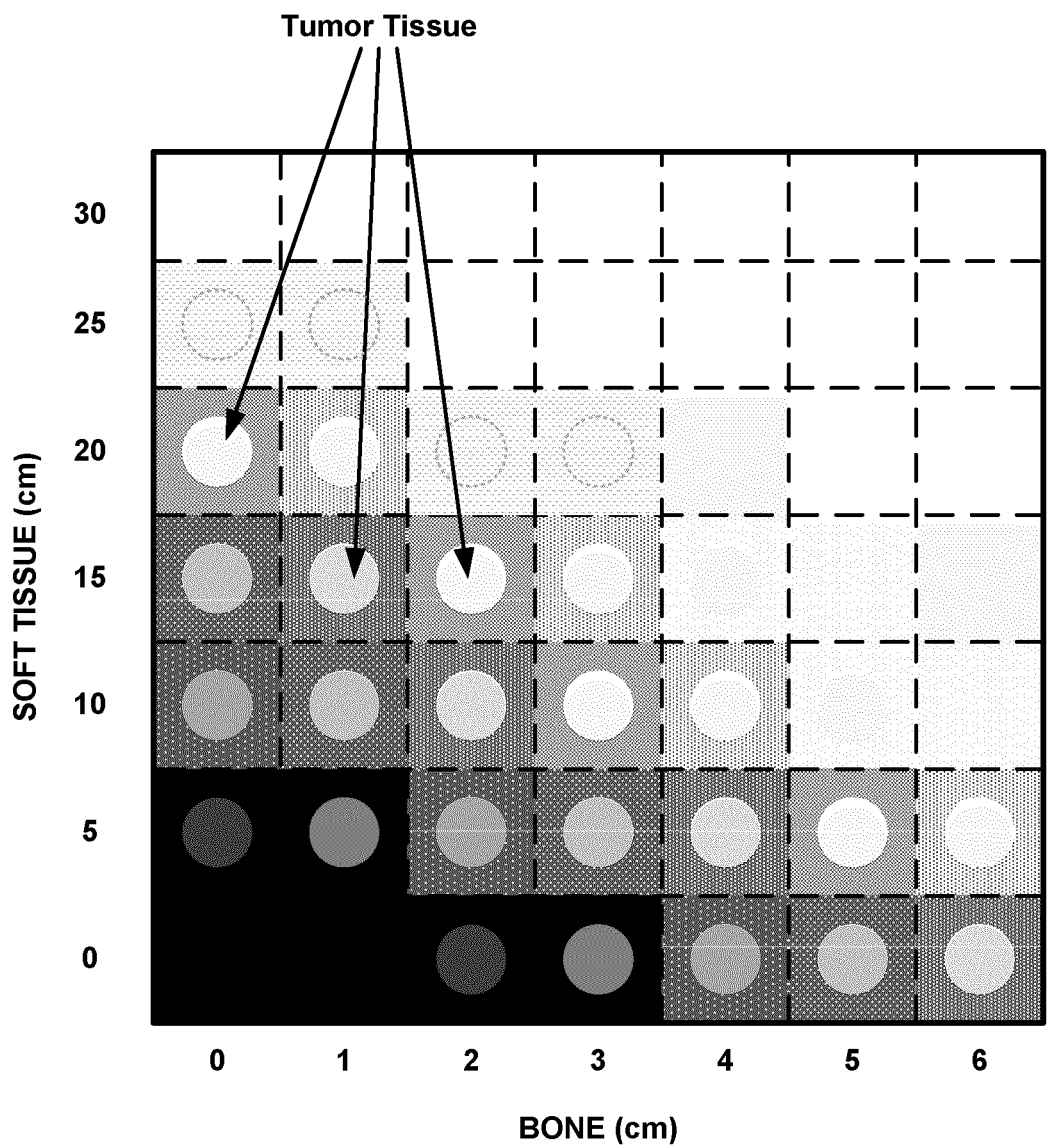
FIG. 5K is an example x-ray image of the step-phantom of FIG. 5J.

FIG. 5K illustrates an example x-ray image of the tissue model shown in FIG. 5J.

FIG. 6 illustrates an example method which generates combined images that use weighting factors optimized for enhancing tumor contrast in a tumor region and weighting factors optimized for deemphasizing bone tissue outside of the tumor region. In block S2, sets of pre-calibrated weighting factors are generated. In block S4, a weighting image for maximizing tumor contrast and de-emphasizing bone is generated. Thicknesses of tissue may, for example, be ascertained using data representative of the imaged tissue region and/or directly from acquired higher and lower energy images of the tissue region as described elsewhere herein. In block S6, higher and lower energy images are acquired, processed and a per-pixel dual energy image (e.g. image 105 described elsewhere herein) is generated.

As one non-limiting example use case, maximizing tumor contrast in areas of the combined image which correspond to tumors while maximally de-emphasizing bone tissue in other areas of the combined image may facilitate precise tumor localization and/or radiation delivery during a course of radiotherapy. As another non-limiting example use case, maximizing tumor contrast while de-emphasizing one or more other tissue types (e.g. bone tissue) may assist with identification of the tumor(s) in diagnostic x-ray imaging.

Another aspect of the invention provides apparatus for dual energy x-ray imaging. The apparatus may comprise a dual energy x-ray imaging system or components for a dual energy x-ray imaging system. One example dual energy x-ray imaging system is illustrated in FIG. 7.

Figure 7:
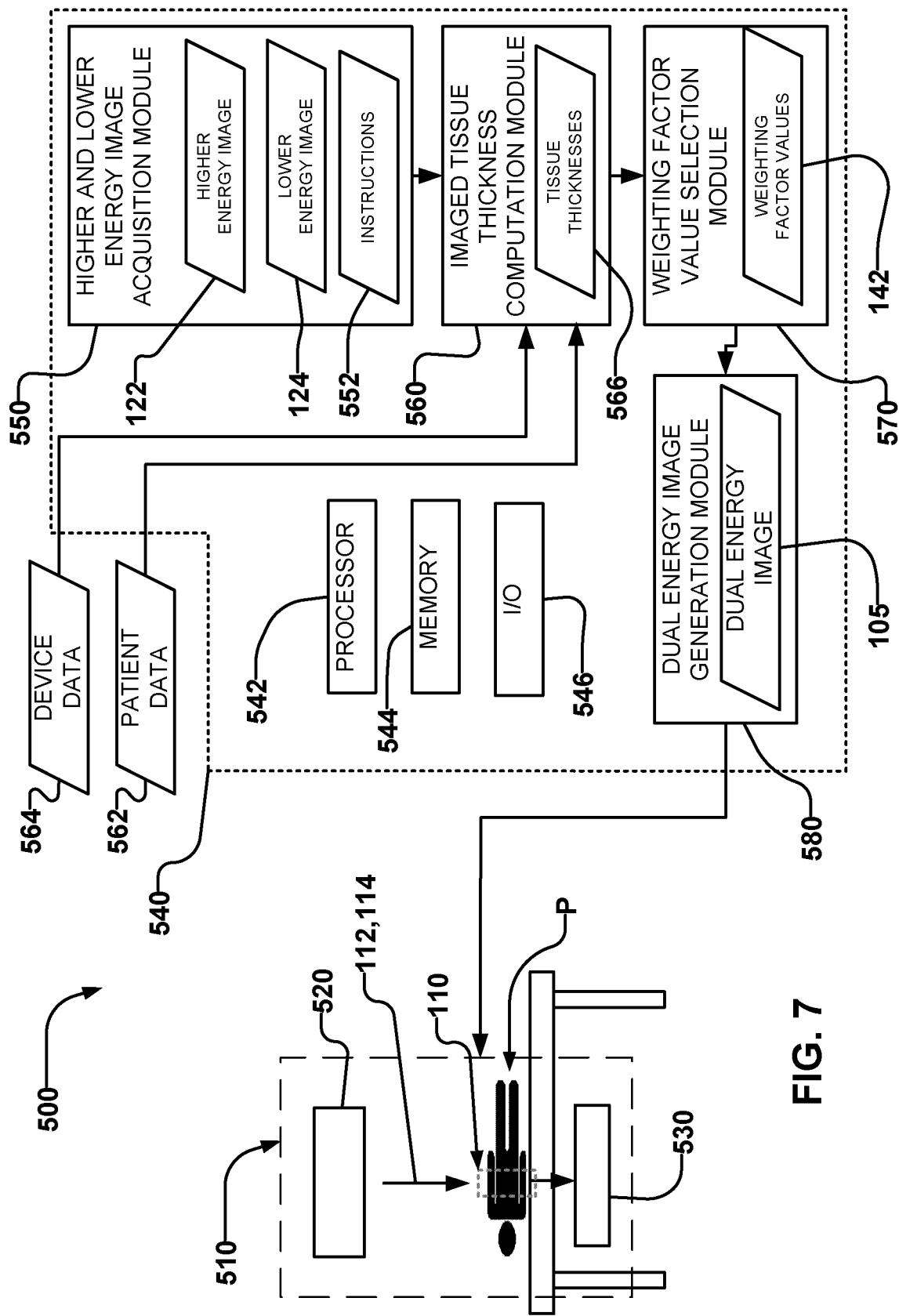
FIG. 7 is a schematic illustration of an x-ray imaging system according to an example embodiment.

FIG. 7 shows an example x-ray imaging system 500 of a type that may be used to generate a dual energy x-ray image 105. The example system 500 includes an x-ray imaging device 510 comprising a radiation source 520 and a detector 530. To image a tissue region 110 of patient P, radiation source 520 may be operated to emit higher and lower energy radiation beams 112, 114 toward patient P.

In some embodiments, x-ray imaging device 510 optionally comprises a plurality of radiation sources 520A and 520B (not expressly shown) which emit radiation beams having different energy values. In such embodiments, radiation sources 520A, 520B may emit higher and lower energy radiation beams 112, 114 respectively.

Radiation source 520 and detector 530 may, for example, be located on opposing sides of patient P. Detector 530 detects a remaining portion of higher and lower energy radiation beams 112, 114 upon radiation beams 112, 114 passing through tissue region 110 of patient P. In some embodiments, detector 530 may comprise a Cesium Iodide scintillator. In some embodiments, detector 530 comprises enough pixels to get a desired resolution of image 105 as described elsewhere herein. In some embodiments, detector 530 may comprise 512×512 pixels. In some embodiments, detector 530 may, for example, be a commercially available 8-inch PerkinElmer XRD flat panel detector.

In some embodiments, motors, actuators or the like may be used to position radiation source 520 for emitting, and detector 530 for detecting, radiation beams 112, 114 along desired beam paths passing through tissue region 110 of patient P. In some embodiments, radiation source 520 and detector 530 may, for example, be part of a commercially available x-ray imaging device.

System 500 may also include a data processing system such as computer 540. Computer 540 comprises one or more processors 542, memory 544 and I/O (i.e. input/output) interface 546. I/O interface 546 may comprise one or more output devices which permit data to be output from computer 540 to a user (not expressly shown) such as, for example, one or more displays, a printer or the like. I/O interface 546 may also comprise one or more input devices which permit user to provide data to computer 540 such as, for example, a mouse, a keyboard, a touch-screen or the like. In some embodiments I/O interface 546 comprises a network interface for communicating data to and/or from computer 540 via a suitable network.

In some embodiments, computer 540 is configured to generate a dual energy image 105. Generating a dual energy image 105 may comprise, for example, generating instructions to be executed by a control system of x-ray imaging system 510. In some embodiments, computer 540 is configured to control one or more parameters of x-ray imaging system during generation of a dual energy image 105. Such parameters may, for example, include paths of radiation beams 112, 114, x-ray radiation dose, fluence, beam energy, a time period between when a higher energy image 122 is acquired and a lower energy image 124 is acquired or the like.

A data processor such as computer 540 may, for example, comprise a higher and lower energy image acquisition module 550, an imaged tissue thickness computation module 560, a weighting factor value selection module 570 and a dual energy image generation module 580.

Higher and lower energy image acquisition module 550 obtains higher and lower energy x-ray images 122, 124. Module 550 may, for example:
  generate instructions 552 to be executed by a control system of x-ray imaging device 510 to acquire higher and lower energy images 122, 124;
  receive higher and lower energy images 122, 124 from an x-ray imaging device; and/or
  retrieve higher and lower energy images 122, 124 from a data store.

Instructions 552 may, for example, instruct x-ray imaging device 510 to acquire higher and lower energy x-ray images 122, 124 having properties as described elsewhere herein.

Imaged tissue thickness computation module 560 processes patient data 562 together with device data 564 to calculate thicknesses 566 of tissue corresponding to one or more pixels of higher and lower images 122, 124 (e.g. thicknesses of tissue present within an imaged tissue region 110).

Patient data 562 comprises data from which thicknesses 566 of different tissue types within tissue region 110 may be ascertained. Patient data 562 may be of any type described elsewhere herein. In some embodiments, patient data 562 may be obtained from memory 544. In some embodiments, patient data 562 is provided using I/O interface 546.

Device data 564 relates to the capabilities of an x-ray imaging device (e.g. device 510). Device data 564 may, for example, include:
information regarding the orientation of radiation source 520 and detector 530 of a device 510;
information regarding the beam's eye view of radiation source 520;
etc.

Weighting factor value selection module 570 processes tissue thicknesses 566 to determine weighting factor values 142 to be applied in combining higher or lower energy images 122, 124. Weighting factor value selection module 570 may, for example, access memory 544 or a suitable lookup device to determine weighting factor values 142. In some embodiments weighting factor value selection module 570 is configured to perform interpolation between stored optimal weighting factor values for different tissue thicknesses to obtain an optimal weighting value for use with tissue thicknesses 566.

Dual energy image generation module 580 combines higher and lower images 122, 124 using weighting factor values 142 to generate dual energy image 105. Dual energy image 105 may, for example, be output to user using I/O interface 546. Dual energy image 105 may be distributed, for example, using the network interface. In some embodiments, dual energy image 105 may be recorded in memory 544.

An x-ray imaging system that implements aspects of the present technology may incorporate user controls which allow a user to adjust how combined x-ray images are created. Examples of controls that may be provided are:

A mode selection control or controls that allows a user to select among imaging modes. A mode selection control may, for example allow selection among: a per-pixel dual energy imaging mode as described herein (which uses weighting factors determined on a pixel-by-pixel or area by area basis based on tissue thicknesses or other factors), and one or more of a single energy imaging mode, a conventional dual energy imaging mode (which uses a single weighting factor for creating a combined image). In an example embodiment the mode selection control allows a user to select among plural modes including (a) conventional dual energy imaging (b) Per pixel dual energy imaging that cancels bone and (c) Per pixel dual energy imaging that cancels bone and enhances tumor contrast.

A weighting factor selection control or controls that allow a user to select weighting factors to be used. For example for per-pixel dual energy imaging the weighting factor selection control may allow selection among: weighting factors that have been selected for various goals such as deemphasizing bone tissue, deemphasizing soft tissue, enhancing contrast of tumors, etc.). Weighting factor control(s) may allow fine adjustment of weighting factors. For example, where a user has chosen to use weighting factors selected to enhance contrast of tumor tissue the weighting factor controls may include a control that allows adjustment of the weighting factors to most effectively enhance contrast for a particular thickness of tumor tissue (as seen in FIGS. 5H and 5I the value of a weighting factor optimized for enhancing tumor contrast depends both on the thicknesses of tissues present but also on thickness of the tumor tissue). The weighting factor selection control(s) may allow selection among: basing weighting factors on previously obtained imaging data (e.g. CT or MRI images), basing weighting factors on data from the higher and lower energy x-ray images, basing weighting factors on physical dimensions of a patient and/or on a blend of two or more of these.

A control or controls that allow a user to select different sources of weighting factors for different portions of an image. These controls may allow the user to: select the weighting factors to be used; select the portions of the image; and/or select how the weighting factors transition near boundaries of the portions of the image. For example, to avoid sharp changes in the boundaries of portions of the image (e.g. near the boundary of a portion of the image which includes tumor tissue) the weighting (ω) values may smoothly vary from one source of weighting factor to another as described herein. The user may be able to adjust the thickness of the boundary regions (margins) and/or the level of smoothness in a linear or non-linear fashion (as described elsewhere herein).

A control or controls that allow a user to select a mechanism for generating weighting factors. For example, such a control or controls may allow a user to select among:
selecting among various goals for the weighting factors (e.g. deemphasize bone, deemphasize soft tissue, deemphasize some particular type of soft tissue, enhance contrast of some type of tissue e.g. tumor tissue, etc.)
calculating weighting factors based on tissue thicknesses;
where the weighting factors are calculated, optionally selecting among two or more models for calculating the weighting factors. For example, such a control may allow selection among: one or more theoretical computations for determining weighting factors; selecting and/or interpolating between experimentally determined weighting factors (e.g. weighting factors determined by processing images of a step phantom as described herein)
Selecting a source for tissue thickness measurements (e.g. a CT or MRI scan, acquired images 122, 124, etc.);
Selecting a previously determined weighting factor image. This option may, for example, be useful where it is desired: to compare dual energy x-ray images for the same patient taken at different times, to expedite generation of a dual energy image 105, to reduce patient exposure to radiation (e.g. reduce how many CT scans a patient may need to have), and/or to reduce patient inconvenience (e.g. reduce how many imaging procedures a patient may need to have), etc. Where this option is selected the weighting factor image should be registered to the higher and lower energy x-ray images to be combined. Since the previously determined weighting factor image is registered to previously obtained higher and lower energy x-ray images the previously determined weighting factor image may be registered to newly acquired higher and lower energy x-ray images using the same transform that will register the previously acquired higher or lower energy x-ray image to the corresponding newly acquired higher or lower energy x-ray image.

A control or controls that allow a user to set the resolution with which weighting factors are set. For example, weighting factors may be set separately for every pixel, for blocks of a few pixels (e.g. 4 or 9 or 25 pixels), for larger regions within the image, etc. Optionally the resolution with which weighting factors are set can differ across the image. For example, the controls may allow a user to specify a region of special interest in which weighting factors are specified at a higher resolution (e.g. weighting factor(s) for each pixel). Outside of the region of special interest weighting factors may be specified at a lower resolution (for example, for each group of pixels or a constant weighting factor for the entire area outside the region of special interest).

In some embodiments, one or more data processors included in system 500 are configured to perform any of the methods described herein. For example, computer 540 may be configured to perform method 100 described herein.

In some embodiments, the methods and apparatus described herein may be used to generate dual energy images 105 showing tissue which would otherwise be obstructed by anatomical noise (e.g. ribs 22). For example, dual energy images 105 may be generated to view a lung tumor which is otherwise obstructed from view by rib bone. Using the methods and apparatus described herein, generated dual energy images 105 may de-emphasize both ribs and vertebrae.

In some embodiments, the methods and apparatus described herein may be used to track progress of a medical procedure being administered to patient P. For example, generated dual energy images 105 may be used to track the impact of a course of radiation treatment on a target tissue contained within patient P, to track the location of the target tissue so radiation is delivered only when the target tissue is at specific locations, track the location of the target tissue to steer delivery of radiation during the course of radiation treatment, or the like. In some embodiments, the methods and apparatus described herein may be used to assist with a medical procedure. For example, generated dual energy images 105 may be used to track the insertion of a catheter into patient P that would otherwise be obstructed from view by anatomical noise (e.g. ribs 22).

Figure 8:
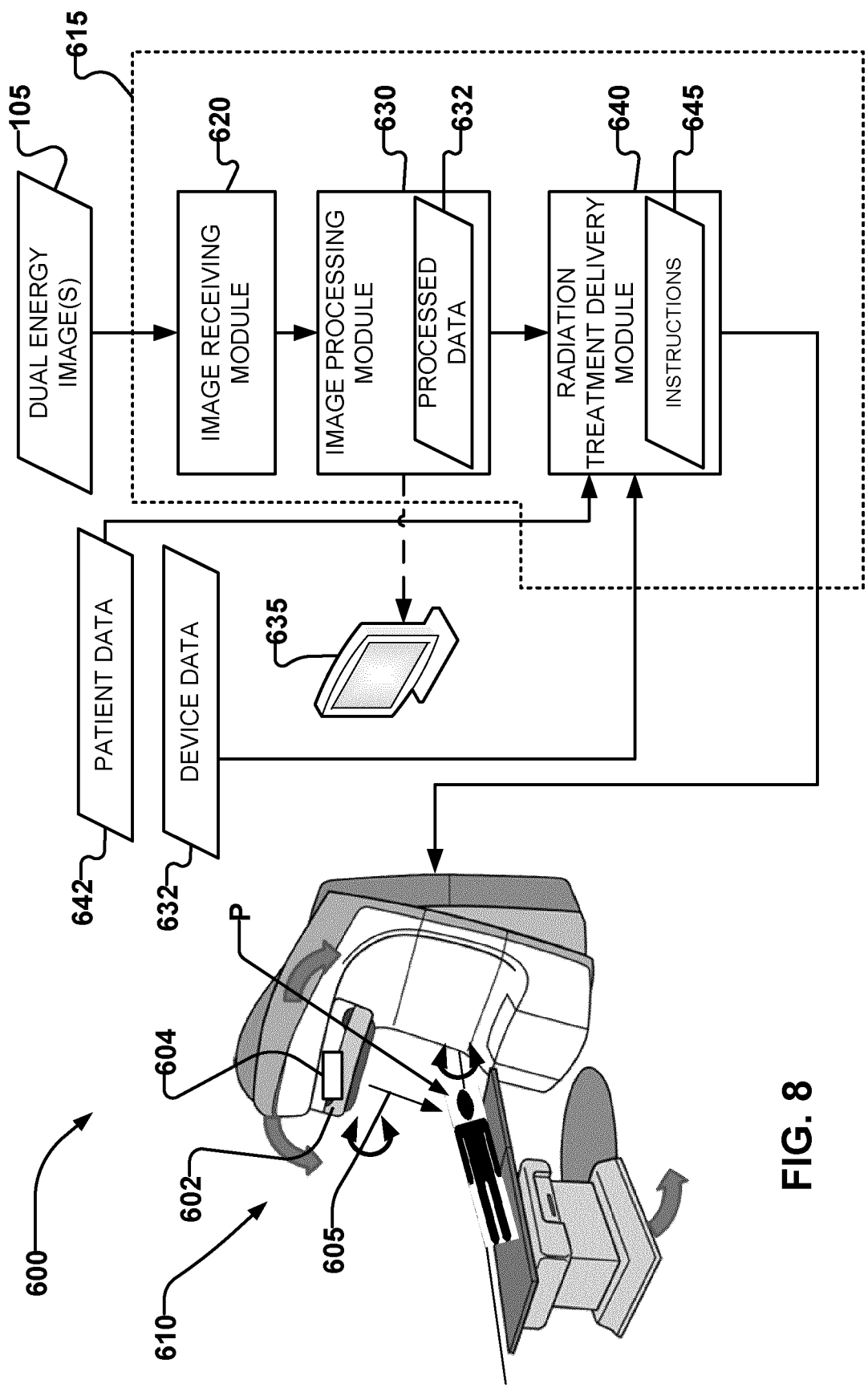
FIG. 8 is a schematic illustration of a radiation therapy system according to an example embodiment.

In some embodiments, generated dual energy images 105 may be used by a radiation therapy system to control delivery of radiation during a course of radiation therapy. FIG. 8 illustrates an example system 600.

Radiation therapy system 600 comprises a radiation delivery device 610. Device 610 comprises a radiation source 604 supported on a gantry 602. Radiation source 604 may, for example, comprise a linear accelerator. Radiation source 604 may be controllable to emit a radiation beam 605 toward patient P. Device 610 may include motors or the like connected to move radiation source 604 relative to patient P. In the illustrated embodiment, gantry 602 may be rotated, thereby rotating the point of origin of radiation beam 605 in an arc around patient P.

Device 610 may take different forms which provide for motion of radiation source 604 relative to patient P. For example, device 610 may comprise a linear accelerator or other radiation source having a rotatable gantry or a robotic radiosurgery system such as a Cyberknife™ system. Different types of device 610 may provide different mechanisms for shaping a path along which radiation beam 605 is emitted. Device 610 may, for example, be a commercially available device from companies such as Varian or Elekta.

System 600 also comprises modules 615 comprising an image receiving module 620, an image processing module 630 and a radiation treatment delivery module 640.

Image receiving module 620 receives one or more generated dual energy images 105 of tissue region 110. The received dual energy images 105 may, for example, be generated using any of the methods and/or apparatus described elsewhere herein. In some embodiments, image receiving module 620 receives images 105 in real time. In some embodiments, images 105 are retrieved from memory 664 (not expressly shown). In some embodiments, images 105 are provided using a network interface operable to communicate data to and/or from system 600 via a suitable network.

The received dual energy images 105 are processed using image processing module 630. Image processing module 630 locates a target tissue within one or more of the received dual energy images 105 generating processed data 632 corresponding to a location of the target tissue within tissue region 110. In some embodiments, the boundaries of the target tissue are located automatically. For example, edge detection may be used to automatically locate the boundaries of the target tissue. In some embodiments, the boundaries of the target tissue may be manually selected by a user. In some embodiments, the located boundaries of the target tissue are verified. For example, the located boundaries of the target tissue may be output to a user for verification (e.g. using optional display 635). In some embodiments, located boundaries of the target tissue in a plurality of received dual energy images 105 may be used to track movement of the target tissue within tissue region 110.

Radiation treatment delivery module 640 receives processed data 632. Module 640 may also receive patient data 642 and device data 632. Using the received data (e.g. processed data 632, patient data 642 and device data 632), module 640 generates instructions 645. Instructions 645 may be used by radiation delivery device 610 to deliver a course of radiation treatment. Instructions 645 may, for example, control parameters of radiation delivery device 610 such as trajectories of radiation beam 605, radiation dose, settings of a collimator leaf of device 610, fluence, beam energy, timing of when radiation beam 605 is emitted or the like.

Patient data 642 relates to information about a patient undergoing radiation treatment (e.g. patient P). Patient data 642 may include, for example, one or more of:
bounds of tissue region 110;
bounds of one or more tissue regions at risk of being exposed to radiation from radiation beam 605;
outer bounds of the patient;
patient demographical information (e.g. age, gender, etc.); etc.

Device data 644 relates to the capabilities of a radiation delivery device (e.g. device 610). Device data 644 may include, for example, one or more of:
a model of a radiation beam shaper provided by device 610 (e.g. a multi-leaf collimator);
information regarding the degrees of freedom provided by device 610 for motion of radiation source 604;
information regarding the capabilities of device 610 such as maximum and minimum beam energies that may be emitted by radiation source 604, how quickly a configuration of device 610 can be changed relative to different axes or other degrees of freedom or the like; etc.

In some embodiments, radiation delivery device 610 comprises x-ray imaging system 500 described elsewhere herein.

Figure 9:
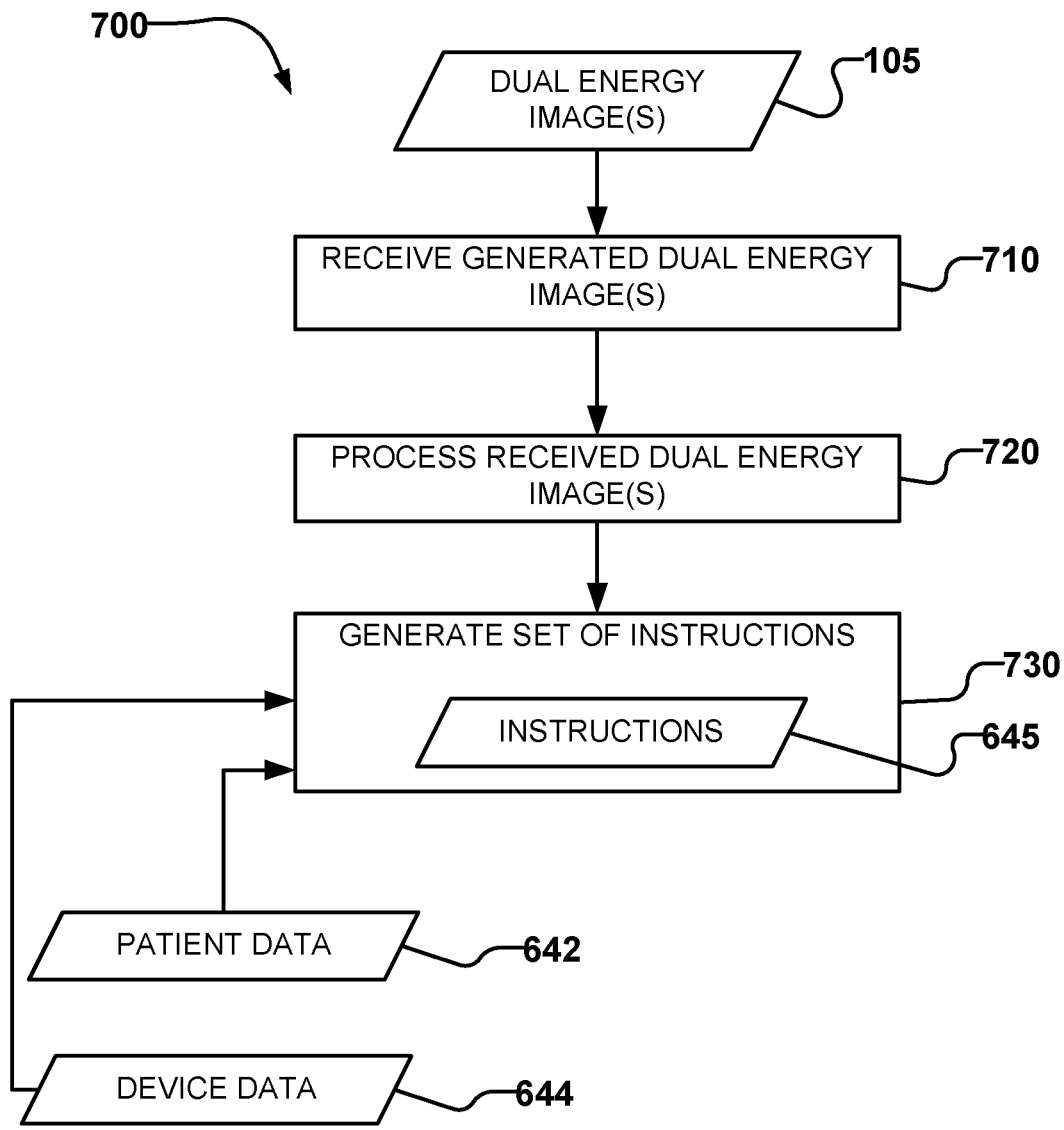
FIG. 9 is a flow chart illustrating a method according to an example embodiment.

FIG. 9 is a flowchart illustrating an example method 700 for controlling delivery of a course of radiation treatment using one or more generated dual energy images 105.

In block 710, one or more generated dual energy images 105 are received. The received dual energy images 105 may, for example, be generated using any of the methods and/or apparatus described elsewhere herein. In block 720, the received dual energy images 105 are processed to locate boundaries of a target tissue (i.e. the tissue the course of radiation treatment will be applied to) contained within the received images 105. As described elsewhere herein, boundaries of the target tissue may be located automatically or manually, and the located boundaries may be verified. In block 730, the located boundaries are used to generate a set of instructions 645 that may be used to control a radiation delivery device (e.g. device 610 described elsewhere herein). The instructions may, for example, cause the radiation delivery device to inhibit delivery of therapy radiation if the target tissue has moved away from a predetermined location by more than a threshold amount.

The instructions may also, for example, cause movement of the treatment couch to align the target tissue with a radiation field (e.g. a radiation field corresponding to beam 605, etc.). In some embodiments the treatment couch is aligned prior to delivery of a course of radiation therapy. In some embodiments the treatment couch is dynamically aligned during the delivery of a course of radiation therapy. In some embodiments the treatment couch is aligned both prior to delivery of a course of radiation treatment and during the course of radiation treatment. In some embodiments, block 730 may also use patient data 642 and/or device data 644 to generate instructions 645.

Some embodiments allow combinations of a plurality of different dual energy imaging modes (e.g. combinations of the modes described above) to be used. In some such embodiments different modes are applied to generate different regions of a dual energy image and/or to generate different dual energy images. For example, a dual energy image of a tissue region (e.g. a patient's thorax) may be quickly generated using a conventional dual energy imaging mode as described above (e.g. by applying a single weighting factor). A higher quality dual energy image of a sub-region of interest (e.g. the patient's right lung region) may use variable weighting factors as described herein. The higher quality dual energy image may, for example, be generated using a per pixel dual energy imaging mode as described elsewhere herein. In some embodiments the sub-region of interest is user selected. In such embodiments the sub-region may, for example, be selected by user interaction with an interface (e.g. a GUI) such as by positioning a view finder over the sub-region of interest, drawing a perimeter around the sub-region of interest, etc.

In some embodiments the sub-region is selected with reference to volumetric data representative of the tissue region (e.g. CT data, MRI data, etc.). In some such embodiments a method of ray tracing associates the selected sub-region with a corresponding region in the acquired higher and lower energy images. The sub-region may, for example correspond to a region containing tumor tissue or another structure or tissue of interest. In some embodiments the higher quality dual energy image of the sub-region of interest is magnified relative to the quickly generated dual energy image.

In all cases where the systems and methods described herein have been illustrated with reference to a specific example tissue type or types (e.g. tumor tissue), the systems and methods may also be applied to any other tissue type(s).

Interpretation of Terms

Unless the context clearly requires otherwise, throughout the description and the

- "comprise", "comprising", and the like are to be construed in an inclusive sense, as opposed to an exclusive or exhaustive sense; that is to say, in the sense of "including, but not limited to".
- "connected", "coupled", or any variant thereof, means any connection or coupling, either direct or indirect, between two or more elements; the coupling or connection between the elements can be physical, logical, or a combination thereof; elements which are integrally formed may be considered to be connected or coupled.
- "herein", "above", "below", and words of similar import, when used to describe this specification, shall refer to this specification as a whole, and not to any particular portions of this specification.
- "or", in reference to a list of two or more items, covers all of the following interpretations of the word: any of the items in the list, all of the items in the list, and any combination of the items in the list.
- "isocentre" means a point in space through which a radiation beam's central rays pass.
- the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a computer system for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

For example, while processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

In addition, while elements are at times shown as being performed sequentially, they may instead be performed simultaneously or in different sequences. It is therefore intended that the following claims are interpreted to include all such variations as are within their intended scope.

Embodiments of the invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Where a record, field, entry, and/or other element of a database is referred to above, unless otherwise indicated, such reference should be interpreted as including a plurality of records, fields, entries, and/or other elements, as appropriate. Such reference should also be interpreted as including a portion of one or more records, fields, entries, and/or other elements, as appropriate. For example, a plurality of "physical" records in a database (i.e. records encoded in the database's structure) may be regarded as one "logical" record for the purpose of the description above and the claims below, even if the plurality of physical records includes information which is excluded from the logical record.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

Various features are described herein as being present in "some embodiments" or "in an example embodiment". Such features are not mandatory and may not be present in all embodiments. Embodiments of the invention may include zero, any one or any combination of two or more of such features. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible).

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A method for dual energy x-ray imaging, the method comprising:
acquiring first and second images of a tissue region comprising a first tissue type having a first density and a second tissue type having a second density, the first image corresponding to a first radiation beam having a first energy spectrum and the second image corresponding to a second radiation beam having a second energy spectrum different from the first energy spectrum; and
combining the first and second images to generate a combined image by, separately for each of multiple parts of the first and second images, determining a weighting factor corresponding to the part based on determining a thickness of tissue of each of at least two classes corresponding to the part and pixelwise combining the first and second images using the weighting factors, wherein each of the parts of the first and second images is one pixel.

2. The method according to claim 1 wherein combining the first and second images comprises computing a weighted difference of logarithms of pixels values in the first and second images by performing the computation:

$$\ln(I_{DE})=\ln(I_{HE})-\omega \ln(I_{LE}),$$

or a mathematical equivalent thereof, wherein $I_{HE}$ represents pixel values in the first image, $I_{LE}$ represents pixel values in the second image, $\omega$ represents the weighting factors and $I_{DE}$ represents pixel values in the combined image.

3. The method according to claim 1 wherein combining the first and second images comprises applying a non-rigid transformation to at least one of the first and second images.

4. The method according to claim 1 wherein determining the thickness of tissue of each of the at least two classes comprises processing volumetric data for each tissue region by ray tracing, the volumetric data obtained by CT scan.

5. The method according to claim 1 wherein determining the thickness of tissue of each of the at least two classes comprises processing CT data to classify voxels of the CT data into the at least two classes based on densities indicated by the CT data for the voxels, generating a volumetric mask for each of the at least two classes, each volumetric mask comprising data indicating for voxels of the volumetric mask whether the voxel does or does not correspond to tissue of the corresponding class, and processing the volumetric masks.

6. The method according to claim 5 wherein processing the volumetric masks comprises computing digitally reconstructed radiographs (DRRs) for each of the volumetric masks from the point of view of the first and second images.

7. The method according to claim 6 wherein processing the volumetric masks is based on a geometry of the first and second radiation beams and comprises determining the thickness of tissue of each of the at least two classes along rays of the first and second radiation beams corresponding to pixels of the first and second images.

8. The method according to claim 1 comprising applying the thickness of tissue of each of the at least two classes as inputs to a calculation to compute the weighting factor for each of the parts.

9. The method according to claim 1 comprising using the thickness of tissue of each of the at least two classes as keys to retrieve the weighting factor for each of the parts from a lookup table.

10. The method according to claim 1 comprising acquiring one or more dark images of the tissue model; and pixelwise subtracting the one or more dark images from each of the first and second images of the tissue model.

11. The method according to claim 1 comprising acquiring at least one of first and second flood images, the flood images respectively corresponding to the first and second radiation beams and pixelwise dividing at least the first image of the tissue model with the first flood image or the second image of the tissue model with the second flood image.

12. The method according to claim 1 comprising:
identifying a region of interest;
wherein determining the weighting factors comprises:
for pixels within the region of interest selecting the weighting factors that cause increased contrast for a first selected tissue type; and
for pixels outside of the region of interest selecting the weighting factors that cause de-emphasis for a second selected tissue type.

13. The method according to claim 12 wherein determining the weighting factors comprises:
for pixels within the region of interest using a first algorithm to determine the weighting factors; and
for pixels outside of the region of interest using a second algorithm different from the first algorithm to determine the weighting factors.

14. The method according to claim 12 wherein determining the weighting factors comprises:
for pixels within the region of interest selecting weighting factors from a first set of weighting factors; and
for pixels outside of the region of interest selecting the weighting factors from a second set of weighting factors.

15. An x-ray imaging method comprising:
acquiring a first image of a tissue region by controlling a radiation source to emit a first radiation beam having a first energy range;
acquiring a second image of the tissue region by controlling the radiation source to emit a second radiation beam having a second energy range wherein a maximum energy of the second energy range is lower than a maximum energy of the first energy range;
classifying tissues having a density greater than a threshold density in a first one of plural density ranges and classifying tissues having density less than the threshold density in a second one of the plural density ranges;
for each pixel of the first and second images, determining amounts of tissue in each of the first and second ones of the plural density ranges lying on a ray extending between the radiation source and a location on a detector used to acquire the pixel of the first and second images and determining a weighting factor for each pixel based on the amounts;
pixelwise combining the first and second images to generate a combined image by, separately for each pixel of the combined image, combining corresponding pixels of the first and second images using the corresponding one of the weighting factors.

16. The method according to claim 15 wherein combining the first and second images comprises computing a weighted difference of logarithms of pixels values in the first and second images by performing the computation:

$$\ln(I_{DE})=\ln(I_{HE})-\omega \ln(I_{LE}),$$

or a mathematical equivalent thereof, wherein $I_{HE}$ represents pixel values in the first image, $I_{LE}$ represents pixel values in the second image, $\omega$ represents the weighting factors and $I_{DE}$ represents pixel values in the combined image.

17. The method according to claim 15 wherein determining the amount of tissue in each of the plural density ranges comprises processing volumetric data for the tissue region.

18. The method according to claim 17 wherein the volumetric data comprises computed tomography (CT) data and determining the amount of tissue in each of the plural density ranges comprises processing the CT data to classify voxels of the CT data into the plural density ranges based on densities indicated by the CT data for the voxels, generating a volumetric mask for each of the plural density ranges, each volumetric mask comprising data indicating for voxels of the volumetric mask whether the voxel does or does not correspond to tissue of the corresponding density range, and processing the volumetric masks.

19. The method according to claim 18 wherein processing the volumetric masks comprises computing digitally reconstructed radiographs (DRRs) for each of the masks from the point of view of the first and second images.

20. The method according to claim 19 wherein processing the volumetric masks is based on a geometry of the first and second radiation beams and comprises determining the thickness of tissue of each of the at least two classes along rays of the first and second radiation beams corresponding to pixels of the first and second images.

21. The method according to claim 15 comprising:
identifying a region of interest;
wherein determining the weighting factors comprises:
for pixels within the region of interest selecting the weighting factors that cause increased contrast for a first selected tissue type; and
for pixels outside of the region of interest selecting the weighting factors that cause de-emphasis for a second selected tissue type.

22. The method according to claim 21 wherein determining the weighting factors comprises:
for pixels within the region of interest using a first algorithm to determine the weighting factors; and
for pixels outside of the region of interest using a second algorithm different from the first algorithm to determine the weighting factors.

23. The method according to claim 21 comprising, for pixels in a margin along a boundary of the region of interest for pixels within the region of interest selecting the weighting factors by blending the weighting factors that cause increased contrast for a first selected tissue type and the weighting factors that cause de-emphasis for a second selected tissue type.

24. A dual-energy x-ray imaging system, the system comprising:
an x-ray imaging device comprising a radiation source and a radiation detector;
an image acquisition module, the image acquisition module configured to generate instructions instructing the x-ray imaging device to acquire a first image of a tissue region using a first radiation beam having a first energy range and to acquire a second image of the tissue region using a second radiation beam having a second energy range, the second energy range lower than the first energy range;
an imaged tissue thickness computation module, the image tissue thickness module configured to compute a thickness of tissue of each of at least two classes corresponding to each of multiple pixels of the first and second images;
a weighting factor selection module, the weighting factor selection module configured to determine, for each pixel, a weighting factor based at least in part on the thicknesses of tissue of each of at least two classes corresponding to the pixel; and
a dual energy image generation module, the dual energy image generation module configured to combine the first and second images to generate a combined image by, separately for each of the multiple pixels of the first and second images, pixelwise combining the first and second images using the determined weighting factor.

* * * * *